(12) United States Patent
Meyer et al.

(10) Patent No.: US 8,932,340 B2
(45) Date of Patent: Jan. 13, 2015

(54) BIFURCATED STENT AND DELIVERY SYSTEM

(75) Inventors: Michael P. Meyer, Richfield, MN (US);
Michael W. Davis, Rockford, MN (US);
Benjamin Arcand, Minneapolis, MN (US); Jay Rassat, Buffalo, MN (US);
James Anderson, Fridley, MN (US);
Derek Sutermeister, Eden Prairie, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1161 days.

(21) Appl. No.: 12/129,372

(22) Filed: May 29, 2008

(65) Prior Publication Data

US 2009/0299460 A1    Dec. 3, 2009

(51) Int. Cl.
| | |
|---|---|
| *A61F 2/06* | (2013.01) |
| *A61F 2/856* | (2013.01) |
| *A61F 2/91* | (2013.01) |
| *A61F 2/915* | (2013.01) |
| *A61F 2/954* | (2013.01) |
| *A61F 2/958* | (2013.01) |
| A61M 25/10 | (2013.01) |

(52) U.S. Cl.
CPC . *A61F 2/856* (2013.01); *A61F 2/91* (2013.01);
*A61F 2/915* (2013.01); *A61F 2/954* (2013.01);
*A61F 2/958* (2013.01); A61M 2025/1013 (2013.01)
USPC .......................................... 623/1.11

(58) Field of Classification Search
USPC ............................ 604/96.01, 101.01–101.05,
604/103.06–103.08, 284; 606/108, 153,
606/191–192, 194–195, 198;
623/1.11–1.12, 1.23, 1.35, 1.15
See application file for complete search history.

(56) References Cited

U.S. PATENT DOCUMENTS

| | | | |
|---|---|---|---|
| 4,309,994 | A | 1/1982 | Grunwald |
| 4,445,892 | A | 5/1984 | Hussein et al. |
| 4,649,914 | A | 3/1987 | Kowalewski |
| 4,769,005 | A | 9/1988 | Ginsburg et al. |
| 4,774,949 | A | 10/1988 | Fogarty |
| 4,896,670 | A | 1/1990 | Crittenden |
| 4,905,667 | A | 3/1990 | Foerster et al. |
| 4,906,244 | A | 3/1990 | Pinchuk et al. |
| 4,935,190 | A | 6/1990 | Tennerstedt |
| 4,994,071 | A | 2/1991 | MacGregor |

(Continued)

FOREIGN PATENT DOCUMENTS

| | | |
|---|---|---|
| CA | 2220864 | 7/1999 |
| DE | 9014845 | 2/1991 |

(Continued)

OTHER PUBLICATIONS

U.S. Appl. No. 60/844,011, filed Sep. 12, 2006; Inventor: Broome et al.

(Continued)

*Primary Examiner* — Ashley Fishback
(74) *Attorney, Agent, or Firm* — Vidas, Arrett & Steinkraus, P.A.

(57) ABSTRACT

A delivery system has a stent and a balloon. The stent has a first section made of a plurality of interconnected framework members which define a plurality of potential side branches. The balloon is a dual lumen balloon that can inflate from the proximal end to the distal end with a plurality of protrusions and/or herniations.

11 Claims, 17 Drawing Sheets

(56) References Cited

U.S. PATENT DOCUMENTS

| | | |
|---|---|---|
| 5,037,392 A | 8/1991 | Hillstead |
| 5,053,007 A | 10/1991 | Euteneuer |
| 5,087,246 A | 2/1992 | Smith |
| 5,108,414 A | 4/1992 | Enderle et al. |
| 5,112,900 A | 5/1992 | Buddenhagen et al. |
| 5,147,302 A | 9/1992 | Euteneuer et al. |
| 5,163,989 A | 11/1992 | Campbell et al. |
| 5,209,799 A | 5/1993 | Vigil |
| 5,226,887 A | 7/1993 | Farr et al. |
| 5,306,246 A | 4/1994 | Sahatijian et al. |
| 5,318,587 A | 6/1994 | Davey |
| 5,342,307 A | 8/1994 | Euteneuer et al. |
| 5,342,387 A | 8/1994 | Summers |
| 5,348,538 A | 9/1994 | Wang et al. |
| 5,350,361 A | 9/1994 | Tsukashima et al. |
| 5,358,475 A | 10/1994 | Mares et al. |
| 5,387,235 A | 2/1995 | Chuter |
| 5,403,340 A | 4/1995 | Wang et al. |
| 5,447,497 A | 9/1995 | Sogard et al. |
| 5,456,666 A | 10/1995 | Campbell et al. |
| 5,456,712 A | 10/1995 | Maginot |
| 5,458,572 A | 10/1995 | Campbell et al. |
| 5,476,471 A | 12/1995 | Shifrin et al. |
| 5,478,319 A | 12/1995 | Campbell et al. |
| 5,487,730 A | 1/1996 | Marcadis et al. |
| 5,523,092 A | 6/1996 | Hanson et al. |
| 5,549,552 A | 8/1996 | Peters et al. |
| 5,550,180 A | 8/1996 | Elsik et al. |
| 5,556,383 A | 9/1996 | Wang et al. |
| 5,591,228 A | 1/1997 | Edoga |
| 5,607,444 A | 3/1997 | Lam |
| 5,609,605 A | 3/1997 | Marshall et al. |
| 5,609,627 A | 3/1997 | Goicoechea et al. |
| 5,613,980 A | 3/1997 | Chauhan |
| 5,617,878 A | 4/1997 | Taheri |
| 5,632,762 A | 5/1997 | Myler |
| 5,632,763 A | 5/1997 | Glastra |
| 5,632,772 A | 5/1997 | Alcime et al. |
| 5,636,641 A | 6/1997 | Fariabi |
| 5,669,924 A | 9/1997 | Shaknovich |
| 5,669,932 A | 9/1997 | Fischell et al. |
| 5,676,697 A | 10/1997 | McDonald |
| 5,683,450 A | 11/1997 | Goicoechea et al. |
| 5,697,971 A | 12/1997 | Fischell et al. |
| 5,707,348 A | 1/1998 | Krogh |
| 5,709,713 A | 1/1998 | Evans et al. |
| 5,718,684 A | 2/1998 | Gupta |
| 5,718,724 A | 2/1998 | Goicoechea et al. |
| 5,720,735 A | 2/1998 | Dorros |
| 5,728,065 A | 3/1998 | Follmer et al. |
| 5,746,745 A | 5/1998 | Abele et al. |
| 5,749,825 A | 5/1998 | Fischell et al. |
| 5,749,890 A | 5/1998 | Shaknovich |
| 5,755,734 A | 5/1998 | Richter et al. |
| 5,755,735 A | 5/1998 | Richter et al. |
| 5,755,771 A | 5/1998 | Penn et al. |
| 5,755,773 A | 5/1998 | Evans et al. |
| 5,755,778 A | 5/1998 | Kleshinski |
| 5,782,906 A | 7/1998 | Marshall et al. |
| 5,800,520 A | 9/1998 | Fogarty et al. |
| 5,810,767 A | 9/1998 | Klein |
| 5,824,036 A | 10/1998 | Lauterjung |
| 5,824,040 A | 10/1998 | Cox et al. |
| 5,827,320 A | 10/1998 | Richter et al. |
| 5,830,182 A | 11/1998 | Wang et al. |
| 5,833,657 A | 11/1998 | Reinhardt et al. |
| 5,843,172 A | 12/1998 | Yan |
| 5,851,464 A | 12/1998 | Davila et al. |
| 5,868,776 A | 2/1999 | Wright |
| 5,868,777 A | 2/1999 | Lam |
| 5,882,334 A | 3/1999 | Sepetka et al. |
| 5,891,108 A | 4/1999 | Leone et al. |
| 5,893,887 A | 4/1999 | Jayaraman |
| 5,906,640 A | 5/1999 | Penn et al. |
| 5,908,448 A | 6/1999 | Roberts et al. |
| 5,922,020 A | 7/1999 | Klein et al. |
| 5,922,021 A | 7/1999 | Jang |
| 5,951,941 A | 9/1999 | Wang et al. |
| 5,961,548 A | 10/1999 | Shmulewitz |
| 5,972,017 A | 10/1999 | Berg et al. |
| 5,972,027 A | 10/1999 | Johnson |
| 6,013,054 A | 1/2000 | Jiun Yan |
| 6,013,055 A | 1/2000 | Bampos et al. |
| 6,013,091 A | 1/2000 | Ley et al. |
| 6,017,324 A | 1/2000 | Tu et al. |
| 6,017,363 A | 1/2000 | Hojeibane |
| 6,030,414 A | 2/2000 | Taheri |
| 6,033,380 A | 3/2000 | Butaric et al. |
| 6,033,434 A | 3/2000 | Borghi |
| 6,033,435 A | 3/2000 | Penn et al. |
| 6,048,361 A | 4/2000 | Von Oepen |
| 6,056,775 A | 5/2000 | Borghi et al. |
| 6,059,824 A | 5/2000 | Taheri |
| 6,068,655 A | 5/2000 | Seguin et al. |
| 6,071,285 A | 6/2000 | Lashinski et al. |
| 6,071,305 A | 6/2000 | Brown et al. |
| 6,086,611 A | 7/2000 | Duffy et al. |
| 6,093,203 A | 7/2000 | Uflacker |
| 6,096,070 A | 8/2000 | Ragheb et al. |
| 6,096,073 A | 8/2000 | Webster et al. |
| 6,099,497 A | 8/2000 | Adams et al. |
| 6,113,579 A | 9/2000 | Eidenschink et al. |
| 6,117,117 A | 9/2000 | Mauch |
| 6,117,156 A | 9/2000 | Richter et al. |
| 6,123,712 A * | 9/2000 | Di Caprio et al. ............ 606/108 |
| 6,123,721 A | 9/2000 | Jang |
| 6,126,652 A | 10/2000 | McLeod et al. |
| 6,129,738 A | 10/2000 | Lashinski et al. |
| 6,129,754 A | 10/2000 | Kanesaka et al. |
| 6,135,982 A | 10/2000 | Campbell |
| 6,142,973 A | 11/2000 | Carleton et al. |
| 6,143,002 A | 11/2000 | Vietmeier |
| 6,146,356 A | 11/2000 | Wang et al. |
| 6,159,238 A | 12/2000 | Killion et al. |
| 6,165,195 A | 12/2000 | Wilson et al. |
| 6,168,621 B1 | 1/2001 | Vrba |
| 6,171,278 B1 | 1/2001 | Wang et al. |
| 6,183,509 B1 | 2/2001 | Dibie |
| 6,190,404 B1 | 2/2001 | Palmaz et al. |
| 6,203,568 B1 | 3/2001 | Lombardi et al. |
| 6,206,915 B1 | 3/2001 | Fagan et al. |
| 6,206,916 B1 | 3/2001 | Furst |
| 6,210,380 B1 | 4/2001 | Mauch |
| 6,210,429 B1 | 4/2001 | Vardi et al. |
| 6,210,433 B1 | 4/2001 | Larre |
| 6,210,436 B1 | 4/2001 | Weadock |
| 6,217,503 B1 | 4/2001 | Weinberger |
| 6,231,598 B1 | 5/2001 | Berry et al. |
| 6,240,616 B1 | 6/2001 | Yan |
| 6,241,762 B1 | 6/2001 | Shanley |
| 6,253,443 B1 | 7/2001 | Johnson |
| 6,254,593 B1 | 7/2001 | Wilson |
| 6,254,632 B1 | 7/2001 | Wu et al. |
| 6,258,099 B1 | 7/2001 | Mareiro et al. |
| 6,258,115 B1 | 7/2001 | Dubrul |
| 6,258,116 B1 | 7/2001 | Hojeibane |
| 6,258,121 B1 | 7/2001 | Yang et al. |
| 6,261,305 B1 | 7/2001 | Marotta et al. |
| 6,261,316 B1 | 7/2001 | Shaolian et al. |
| 6,261,320 B1 | 7/2001 | Tam et al. |
| 6,264,662 B1 | 7/2001 | Lauterjung |
| 6,264,686 B1 | 7/2001 | Rieu et al. |
| 6,273,908 B1 | 8/2001 | Ndondo-Lay |
| 6,273,913 B1 | 8/2001 | Wright et al. |
| 6,280,413 B1 | 8/2001 | Clark et al. |
| 6,287,628 B1 | 9/2001 | Hossainy et al. |
| 6,290,673 B1 | 9/2001 | Shanley |
| 6,293,967 B1 | 9/2001 | Shanley |
| 6,293,968 B1 | 9/2001 | Taheri |
| 6,325,826 B1 | 12/2001 | Vardi et al. |
| 6,328,925 B1 | 12/2001 | Wang et al. |
| 6,334,864 B1 | 1/2002 | Amplatz et al. |
| 6,334,870 B1 | 1/2002 | Ehr et al. |
| 6,346,089 B1 | 2/2002 | Dibie |

(56) References Cited

U.S. PATENT DOCUMENTS

| | | | |
|---|---|---|---|
| 6,348,065 B1 | 2/2002 | Brown et al. |
| 6,355,060 B1 | 3/2002 | Lenker et al. |
| 6,358,552 B1 | 3/2002 | Mandralis et al. |
| 6,361,544 B1 | 3/2002 | Wilson et al. |
| 6,361,555 B1 | 3/2002 | Wilson |
| 6,379,381 B1 | 4/2002 | Hossainy et al. |
| 6,383,213 B2 | 5/2002 | Wilson et al. |
| 6,395,018 B1 | 5/2002 | Castaneda |
| 6,395,020 B1 | 5/2002 | Ley et al. |
| 6,395,326 B1 | 5/2002 | Castro et al. |
| 6,406,457 B1 | 6/2002 | Wang et al. |
| 6,409,741 B1 * | 6/2002 | Crocker et al. .............. 606/192 |
| 6,423,091 B1 | 7/2002 | Hojeibane |
| 6,436,104 B2 | 8/2002 | Hojeibane |
| 6,436,134 B2 | 8/2002 | Richter et al. |
| 6,478,816 B1 | 11/2002 | Kveen et al. |
| 6,488,653 B1 | 12/2002 | Lombardo |
| 6,491,666 B1 | 12/2002 | Santini, Jr. et al. |
| 6,506,437 B1 | 1/2003 | Harish et al. |
| 6,508,836 B2 | 1/2003 | Wilson et al. |
| 6,517,558 B2 | 2/2003 | Gittings et al. |
| 6,520,988 B1 | 2/2003 | Colombo et al. |
| 6,527,762 B1 | 3/2003 | Santini, Jr. et al. |
| 6,527,799 B2 | 3/2003 | Shanley |
| 6,537,256 B2 | 3/2003 | Santini, Jr. et al. |
| 6,540,779 B2 | 4/2003 | Richter et al. |
| 6,551,351 B2 | 4/2003 | Smith et al. |
| 6,551,838 B2 | 4/2003 | Santini, Jr. et al. |
| 6,558,422 B1 | 5/2003 | Baker et al. |
| 6,562,065 B1 | 5/2003 | Shanley |
| 6,579,309 B1 | 6/2003 | Loos et al. |
| 6,579,312 B2 | 6/2003 | Wilson et al. |
| 6,582,394 B1 | 6/2003 | Reiss et al. |
| 6,596,020 B2 | 7/2003 | Vardi et al. |
| 6,599,316 B2 | 7/2003 | Vardi et al. |
| 6,638,302 B1 | 10/2003 | Curcio et al. |
| 6,645,242 B1 | 11/2003 | Quinn |
| 6,652,441 B2 | 11/2003 | Weinberger et al. |
| 6,656,162 B2 | 12/2003 | Santini, Jr. et al. |
| 6,669,683 B2 | 12/2003 | Santini, Jr. et al. |
| 6,689,156 B1 | 2/2004 | Davidson et al. |
| 6,692,483 B2 | 2/2004 | Vardi et al. |
| 6,695,877 B2 | 2/2004 | Brucker et al. |
| 6,706,062 B2 | 3/2004 | Vardi et al. |
| 6,709,379 B1 | 3/2004 | Brandau et al. |
| 6,713,119 B2 | 3/2004 | Hossainy et al. |
| 6,730,064 B2 | 5/2004 | Ragheb et al. |
| 6,749,628 B1 | 6/2004 | Callol et al. |
| 6,758,859 B1 | 7/2004 | Dang et al. |
| 6,764,507 B2 | 7/2004 | Shanley et al. |
| 6,773,429 B2 | 8/2004 | Sheppard, Jr. et al. |
| 6,776,793 B2 | 8/2004 | Brown et al. |
| 6,783,543 B2 | 8/2004 | Jang |
| 6,790,228 B2 | 9/2004 | Hossainy et al. |
| 6,811,566 B1 | 11/2004 | Penn et al. |
| 6,827,250 B2 | 12/2004 | Uhland et al. |
| 6,835,203 B1 | 12/2004 | Vardi et al. |
| 6,858,038 B2 | 2/2005 | Heuser |
| 6,884,258 B2 | 4/2005 | Vardi et al. |
| 6,896,699 B2 | 5/2005 | Wilson et al. |
| 6,904,658 B2 | 6/2005 | Hines |
| 6,932,837 B2 | 8/2005 | Amplatz et al. |
| 6,946,092 B1 | 9/2005 | Bertolino et al. |
| 6,955,687 B2 | 10/2005 | Richter et al. |
| 6,955,688 B2 | 10/2005 | Wilson et al. |
| 6,962,602 B2 | 11/2005 | Vardi et al. |
| 6,989,071 B2 | 1/2006 | Kocur et al. |
| 7,018,400 B2 | 3/2006 | Lashinski et al. |
| 7,041,130 B2 | 5/2006 | Santini, Jr. et al. |
| 7,052,488 B2 | 5/2006 | Uhland |
| 7,056,323 B2 | 6/2006 | Mareiro et al. |
| 7,056,338 B2 | 6/2006 | Shanley et al. |
| 7,060,091 B2 | 6/2006 | Killion et al. |
| 7,070,616 B2 | 7/2006 | Majercak et al. |
| 7,160,321 B2 | 1/2007 | Shanley et al. |
| 7,169,175 B2 | 1/2007 | Cottone, Jr. et al. |
| 7,169,179 B2 | 1/2007 | Shanley et al. |
| 7,179,288 B2 | 2/2007 | Shanley |
| 7,179,289 B2 | 2/2007 | Shanley |
| 7,208,010 B2 | 4/2007 | Shanley et al. |
| 7,208,011 B2 | 4/2007 | Shanley et al. |
| 7,220,275 B2 | 5/2007 | Davidson et al. |
| 2001/0003161 A1 | 6/2001 | Vardi et al. |
| 2001/0004706 A1 | 6/2001 | Hojeibane |
| 2001/0004707 A1 | 6/2001 | Dereume et al. |
| 2001/0012927 A1 | 8/2001 | Mauch |
| 2001/0016766 A1 | 8/2001 | Vardi et al. |
| 2001/0016767 A1 | 8/2001 | Wilson et al. |
| 2001/0016768 A1 | 8/2001 | Wilson et al. |
| 2001/0025195 A1 | 9/2001 | Shaolian et al. |
| 2001/0027291 A1 | 10/2001 | Shanley |
| 2001/0027338 A1 | 10/2001 | Greenberg |
| 2001/0029396 A1 | 10/2001 | Wilson et al. |
| 2001/0037116 A1 | 11/2001 | Wilson et al. |
| 2001/0037138 A1 | 11/2001 | Wilson et al. |
| 2001/0039448 A1 | 11/2001 | Dibie |
| 2001/0049552 A1 | 12/2001 | Richter et al. |
| 2001/0056297 A1 | 12/2001 | Hojeibane |
| 2002/0013618 A1 | 1/2002 | Marotta et al. |
| 2002/0013619 A1 | 1/2002 | Shanley |
| 2002/0022874 A1 | 2/2002 | Wilson |
| 2002/0026232 A1 | 2/2002 | Marotta et al. |
| 2002/0035392 A1 | 3/2002 | Wilson |
| 2002/0038146 A1 | 3/2002 | Harry |
| 2002/0042650 A1 | 4/2002 | Vardi et al. |
| 2002/0052648 A1 | 5/2002 | McGuckin, Jr. et al. |
| 2002/0072790 A1 | 6/2002 | McGuckin, Jr. et al. |
| 2002/0091435 A1 * | 7/2002 | Campbell .................. 623/1.11 |
| 2002/0095208 A1 | 7/2002 | Gregorich et al. |
| 2002/0111675 A1 | 8/2002 | Wilson |
| 2002/0156516 A1 | 10/2002 | Vardi et al. |
| 2002/0156517 A1 | 10/2002 | Perouse |
| 2002/0163104 A1 | 11/2002 | Motsenbocker et al. |
| 2002/0165604 A1 | 11/2002 | Shanley |
| 2002/0173835 A1 | 11/2002 | Bourang et al. |
| 2002/0173840 A1 | 11/2002 | Brucker et al. |
| 2002/0183763 A1 | 12/2002 | Callol et al. |
| 2002/0193872 A1 | 12/2002 | Trout, III et al. |
| 2002/0193873 A1 | 12/2002 | Brucker et al. |
| 2003/0009209 A1 | 1/2003 | Hojeibane |
| 2003/0028233 A1 | 2/2003 | Vardi et al. |
| 2003/0050688 A1 | 3/2003 | Fischell et al. |
| 2003/0055483 A1 | 3/2003 | Gumm |
| 2003/0055491 A1 * | 3/2003 | Wang et al. .............. 604/103.07 |
| 2003/0074047 A1 | 4/2003 | Richter |
| 2003/0083687 A1 | 5/2003 | Pallazza |
| 2003/0093109 A1 | 5/2003 | Mauch |
| 2003/0097169 A1 | 5/2003 | Brucker |
| 2003/0105511 A1 | 6/2003 | Welsh et al. |
| 2003/0114912 A1 | 6/2003 | Sequin et al. |
| 2003/0125791 A1 | 7/2003 | Sequin et al. |
| 2003/0125802 A1 | 7/2003 | Callol et al. |
| 2003/0135259 A1 | 7/2003 | Simso |
| 2003/0163157 A1 | 8/2003 | McMorrow et al. |
| 2003/0167085 A1 | 9/2003 | Shanley |
| 2003/0181923 A1 | 9/2003 | Vardi |
| 2003/0195606 A1 | 10/2003 | Davidson et al. |
| 2003/0199970 A1 | 10/2003 | Shanley |
| 2004/0006381 A1 | 1/2004 | Sequin et al. |
| 2004/0015227 A1 | 1/2004 | Vardi et al. |
| 2004/0044396 A1 | 3/2004 | Clerc et al. |
| 2004/0059406 A1 | 3/2004 | Cully et al. |
| 2004/0068161 A1 | 4/2004 | Couvillon, Jr. |
| 2004/0073294 A1 | 4/2004 | Diaz et al. |
| 2004/0088007 A1 | 5/2004 | Eidenschink |
| 2004/0093071 A1 | 5/2004 | Jang |
| 2004/0117003 A1 | 6/2004 | Ouriel et al. |
| 2004/0122505 A1 | 6/2004 | Shanley |
| 2004/0122506 A1 | 6/2004 | Shanley et al. |
| 2004/0127976 A1 | 7/2004 | Diaz |
| 2004/0127977 A1 | 7/2004 | Shanley |
| 2004/0133268 A1 | 7/2004 | Davidson et al. |
| 2004/0138732 A1 | 7/2004 | Suhr et al. |
| 2004/0138737 A1 | 7/2004 | Davidson et al. |

(56) References Cited

U.S. PATENT DOCUMENTS

| | | | |
|---|---|---|---|
| 2004/0142014 | A1 | 7/2004 | Livack et al. |
| 2004/0143321 | A1 | 7/2004 | Livack et al. |
| 2004/0143322 | A1 | 7/2004 | Livack et al. |
| 2004/0148006 | A1 | 7/2004 | Davidson et al. |
| 2004/0148012 | A9 | 7/2004 | Jang |
| 2004/0172121 | A1 | 9/2004 | Eidenschink et al. |
| 2004/0186560 | A1 | 9/2004 | Alt |
| 2004/0202692 | A1 | 10/2004 | Shanley et al. |
| 2004/0204750 | A1 | 10/2004 | Dinh |
| 2004/0215227 | A1 | 10/2004 | McMorrow et al. |
| 2004/0220661 | A1 | 11/2004 | Shanley et al. |
| 2004/0225345 | A1 | 11/2004 | Fischell et al. |
| 2004/0236408 | A1 | 11/2004 | Shanley |
| 2004/0249449 | A1 | 12/2004 | Shanley et al. |
| 2004/0267352 | A1 | 12/2004 | Davidson et al. |
| 2005/0004656 | A1 | 1/2005 | Das |
| 2005/0010278 | A1 | 1/2005 | Vardi et al. |
| 2005/0015108 | A1 | 1/2005 | Williams et al. |
| 2005/0015135 | A1 | 1/2005 | Shanley |
| 2005/0043816 | A1 | 2/2005 | Datta et al. |
| 2005/0060027 | A1 | 3/2005 | Khenansho et al. |
| 2005/0096726 | A1 | 5/2005 | Sequin et al. |
| 2005/102017 | A1 | 5/2005 | Mattison |
| 2005/0102019 | A1 | 5/2005 | Yadin |
| 2005/0102021 | A1 | 5/2005 | Osborne |
| 2005/0102023 | A1 | 5/2005 | Yadin et al. |
| 2005/0119731 | A1 | 6/2005 | Brucker et al. |
| 2005/0125076 | A1 | 6/2005 | Ginn |
| 2005/0131526 | A1 | 6/2005 | Wong |
| 2005/0149161 | A1 | 7/2005 | Eidenschink et al. |
| 2005/0154442 | A1 | 7/2005 | Eidenschink et al. |
| 2005/0154444 | A1 | 7/2005 | Quadri |
| 2005/0183259 | A1 | 8/2005 | Eidenschink et al. |
| 2005/0187602 | A1 | 8/2005 | Eidenschink |
| 2005/0187611 | A1 | 8/2005 | Ding et al. |
| 2005/0192657 | A1 | 9/2005 | Colen et al. |
| 2005/0209673 | A1 | 9/2005 | Shaked |
| 2005/0222668 | A1 | 10/2005 | Schaeffer et al. |
| 2005/0228483 | A1 | 10/2005 | Kaplan et al. |
| 2005/0273149 | A1 | 12/2005 | Tran et al. |
| 2006/0015134 | A1 | 1/2006 | Trinidad |
| 2006/0034884 | A1 | 2/2006 | Stenzel |
| 2006/0036315 | A1 | 2/2006 | Yadin et al. |
| 2006/0041303 | A1 | 2/2006 | Israel |
| 2006/0045901 | A1 | 3/2006 | Weber |
| 2006/0079956 | A1 | 4/2006 | Eigler et al. |
| 2006/0088654 | A1 | 4/2006 | Ding et al. |
| 2006/0093643 | A1 | 5/2006 | Stenzel |
| 2006/0100686 | A1 | 5/2006 | Bolduc et al. |
| 2006/0122698 | A1 | 6/2006 | Spencer et al. |
| 2006/0173528 | A1 | 8/2006 | Feld et al. |
| 2006/0206188 | A1 | 9/2006 | Weber et al. |
| 2006/0287712 | A1 | 12/2006 | Eidenschink |
| 2007/0005126 | A1 | 1/2007 | Tischler |
| 2007/0050016 | A1 | 3/2007 | Gregorich et al. |
| 2007/0055360 | A1 | 3/2007 | Hanson et al. |
| 2007/0073376 | A1 | 3/2007 | Krolik et al. |
| 2007/0073384 | A1 | 3/2007 | Brown et al. |
| 2007/0100434 | A1 | 5/2007 | Gregorich et al. |
| 2007/0173787 | A1 | 7/2007 | Huang et al. |
| 2007/0173923 | A1 | 7/2007 | Savage et al. |
| 2007/0225796 | A1 | 9/2007 | Yadin |
| 2007/0270935 | A1* | 11/2007 | Newhauser et al. ......... 623/1.11 |
| 2008/0172123 | A1 | 7/2008 | Yadin |

FOREIGN PATENT DOCUMENTS

| | | |
|---|---|---|
| DE | 29701758 | 3/1997 |
| DE | 29701883 | 5/1997 |
| DE | 19921788 | 11/2000 |
| EP | 0479730 | 10/1991 |
| EP | 0565796 | 10/1993 |
| EP | 0751752 | 1/1997 |
| EP | 0783873 | 7/1997 |
| EP | 0804907 | 11/1997 |
| EP | 0479557 | 7/1998 |
| EP | 0876805 | 11/1998 |
| EP | 0880949 | 12/1998 |
| EP | 0891751 | 1/1999 |
| EP | 0895759 | 2/1999 |
| EP | 0904745 | 3/1999 |
| EP | 0937442 | 8/1999 |
| EP | 0950386 | 10/1999 |
| EP | 0347023 | 12/1999 |
| EP | 1031328 | 8/2000 |
| EP | 1031329 | 8/2000 |
| EP | 0883384 | 12/2000 |
| EP | 0862392 | 8/2001 |
| EP | 0808140 | 12/2001 |
| EP | 0884028 | 2/2002 |
| EP | 1190685 | 3/2002 |
| EP | 0897700 | 7/2002 |
| EP | 0684022 | 2/2004 |
| EP | 1157674 | 7/2005 |
| EP | 1031330 | 11/2005 |
| EP | 1070513 | 6/2006 |
| FR | 2678508 | 1/1993 |
| FR | 2740346 | 10/1995 |
| FR | 2756173 | 11/1996 |
| GB | 2337002 | 5/1998 |
| WO | 88/06026 | 8/1988 |
| WO | 94/23787 | 10/1994 |
| WO | 95/21592 | 8/1995 |
| WO | 96/29955 | 10/1996 |
| WO | 96/34580 | 11/1996 |
| WO | 96/41592 | 12/1996 |
| WO | 9638109 A1 | 12/1996 |
| WO | 97/07752 | 3/1997 |
| WO | 97/15346 | 5/1997 |
| WO | 97/16217 | 5/1997 |
| WO | 97/26936 | 7/1997 |
| WO | 97/41803 | 11/1997 |
| WO | 97/45073 | 12/1997 |
| WO | 97/46174 | 12/1997 |
| WO | 98/09670 A2 | 3/1998 |
| WO | 98/19628 | 5/1998 |
| WO | 98/23228 | 6/1998 |
| WO | 98/36709 | 8/1998 |
| WO | 98/36784 | 8/1998 |
| WO | 98/37833 | 9/1998 |
| WO | 98/47447 | 10/1998 |
| WO | 98/48879 | 11/1998 |
| WO | 99/03426 | 1/1999 |
| WO | 99/04726 | 2/1999 |
| WO | 99/15103 | 4/1999 |
| WO | 99/15108 | 4/1999 |
| WO | 99/15109 | 4/1999 |
| WO | 99/23977 | 5/1999 |
| WO | 99/24104 | 5/1999 |
| WO | 99/29262 | 6/1999 |
| WO | 99/34749 | 7/1999 |
| WO | 99/36002 | 7/1999 |
| WO | 99/36015 | 7/1999 |
| WO | 99/44539 | 9/1999 |
| WO | 99/56661 | 11/1999 |
| WO | 99/65419 | 12/1999 |
| WO | 00/07523 | 2/2000 |
| WO | 00/10489 | 3/2000 |
| WO | 00/16719 | 3/2000 |
| WO | 00/27307 | 5/2000 |
| WO | 00/27463 | 5/2000 |
| WO | 00/28922 | 5/2000 |
| WO | 00/44307 | 8/2000 |
| WO | 00/44309 | 8/2000 |
| WO | 00/47134 | 8/2000 |
| WO | 00/48531 | 8/2000 |
| WO | 00/49951 | 8/2000 |
| WO | 00/51523 | 9/2000 |
| WO | 00/57813 | 10/2000 |
| WO | 00/67673 | 11/2000 |
| WO | 00/71054 | 11/2000 |
| WO | 00/71055 | 11/2000 |
| WO | 00/74595 | 12/2000 |

(56) References Cited

FOREIGN PATENT DOCUMENTS

| WO | 01/17577 | 3/2001 |
|---|---|---|
| WO | 01/21095 | 3/2001 |
| WO | 01/21109 | 3/2001 |
| WO | 01/21244 | 3/2001 |
| WO | 01/26584 | 4/2001 |
| WO | 01/35715 | 5/2001 |
| WO | 01/35863 | 5/2001 |
| WO | 01/39697 | 6/2001 |
| WO | 01/39699 | 6/2001 |
| WO | 01/41677 | 6/2001 |
| WO | 01/43665 | 6/2001 |
| WO | 01/43809 | 6/2001 |
| WO | 01/45594 | 6/2001 |
| WO | 01/45785 | 6/2001 |
| WO | 01/49342 | 7/2001 |
| WO | 01/54621 | 8/2001 |
| WO | 01/54622 | 8/2001 |
| WO | 01/58385 | 8/2001 |
| WO | 01/60284 | 8/2001 |
| WO | 01/66036 | 9/2001 |
| WO | 01/70294 | 9/2001 |
| WO | 01/70299 | 9/2001 |
| WO | 01/74273 | 10/2001 |
| WO | 01/89409 | 11/2001 |
| WO | 01/91918 | 12/2001 |
| WO | 01/93781 | 12/2001 |
| WO | 02/00138 | 1/2002 |
| WO | 02/053066 | 7/2002 |
| WO | 02/068012 | 9/2002 |
| WO | 03/007842 | 1/2003 |
| WO | 03/055414 | 7/2003 |
| WO | 03/063924 | 8/2003 |
| WO | 2004/026174 | 4/2004 |
| WO | 2004/026180 | 4/2004 |
| WO | 2005/009295 | 2/2005 |
| WO | 2005/014077 | 2/2005 |
| WO | 2005014077 A2 | 2/2005 |
| WO | 2005/041810 | 5/2005 |
| WO | 2005/122959 | 12/2005 |
| WO | 2006014631 A1 | 2/2006 |
| WO | 2006/028925 | 3/2006 |
| WO | 2006/074476 | 7/2006 |
| WO | 2006/127127 | 11/2006 |
| WO | 2007136637 A1 | 11/2007 |

OTHER PUBLICATIONS

U.S. Appl. No. 09/663,111, filed Sep. 15, 2000; Inventor: Davidson et al.

U.S. Appl. No. 09/614,472, filed Jul. 11, 2000; Inventor: Davidson et al.

U.S. Appl. No. 09/325,996, filed Jun. 4, 1999; Inventor: Vardi et al.

Chevalier, M.D., Bernard, "Placement of Coronary Stents in Bifurcation Lesions by the "Culotte" Technique," The American Journal of Cardiology, vol. 82, pp. 943-949 (Oct. 15, 1998).

Nakamura M.D., Shigeru, "Techniques for Palmaz-Schatz Stent Deployment in Lesions with a Large Side Branch," Catheterization and Cardiovascular Diagnosis, vol. 34, pp. 353-361 (1995).

Caputo, Ronald P., "Stent Jail: A Minimum-Security Prison," The American Journal of Cardiology, vol. 77, pp. 1226-1230 (Jun. 1, 1996).

Colombo, M.D., Antonio, ""Kissing" Stent for Bifurcational Coronary Lesions," Catheterization and Cardiovascular Diagnosis, vol. 30, pp. 327-330 (Dec. 1993).

Carrie, M.D., Didier, ""T"-Shaped Stent Placement: A Technique for the Treatment of Dissected Bifurcation Lesions," Catheterization and Cardiovascular Diagnosis, vol. 37 pp. 311-313 (Mar. 1996).

Katoh, M.D., Osamu, "New Double Wire Technique to Stent Ostial Lesions," Catheterization and Cardiovascular Diagnosis, vol. 40, pp. 400-402 (Apr. 1997).

Lewis, M.D., Bruce E., "Acute procedural results in the treatment of 30 coronary artery bifurcation lesions with a double-wire atherectomy technique for side-branch protection," American Heart Journal, vol. 127:6, pp. 1600-1607 (Jun. 1994).

Yamashita, M.D., PhD., Takehiro, "Birfurcation Lesions: Two Stents Versus One Stent—Immediate and Follow-up Results," Journal of the American College of Cardiology, vol. 35:5, pp. 1145-1151 (Apr. 2000).

Satler, M.D., Lowell F., "Bifurcation Disease: To Treat or Not to Treat," Catheterization and Cardiovascular Interventions, vol. 50, pp. 411-412 (2000).

\* cited by examiner

BIFURCATED STENT AND DELIVERY SYSTEM

CROSS-REFERENCE TO RELATED APPLICATIONS

Not Applicable

STATEMENT REGARDING FEDERALLY SPONSORED RESEARCH

Not Applicable

BACKGROUND OF THE INVENTION

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained is a radially compressed configuration by a sheath and/or catheter, is delivered by a stent delivery system or "introducer" to the site where it is required. The introduce may enter the body from an access location outside the body, such as through the patient's skin, or by a "cut down" technique in which the entry blood vessel is exposed by minor surgical means.

Stents, grafts, stent-grafts, vena cava filters, expandable frameworks, and similar implantable medical devices are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. They may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

Within the vasculature, it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels. Many prior art stents however are not wholly satisfactory for use where the site of desired application of the stent is juxtaposed or extends across a bifurcation in an artery or vein such, for example, as the bifurcation in the mammalian aortic artery into the common iliac arteries.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §156(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

BRIEF SUMMARY OF THE INVENTION

In at least one embodiment, a stent comprises a first section comprising plurality of interconnected framework members defining a plurality of potential side branches. In some embodiments, each of the plurality of potential side branches has the same configuration. In some embodiments, the plurality of potential side branches has a plurality of configurations. In at least one embodiment, the plurality of interconnected framework members comprises at least four serpentine rings and a plurality of connecting members.

In at least one embodiment, the stent further comprises a second section comprising at least one circumferential band of struts, the second section engaged to the first section by at least one connector.

In at least one embodiment, a delivery system comprises a balloon catheter having a dual lumen balloon and a stent disposed about the dual lumen balloon. In some embodiments, the dual lumen balloon has an inner balloon made of non-complaint material and an outer balloon made of compliant material. In other embodiments, the inner balloon is in fluid communication with an inner inflation lumen and the outer balloon is in fluid communication with an outer inflation lumen.

In at least one embodiment, a delivery system comprises a balloon catheter having a balloon that progressively inflates from the proximal end to the distal end.

In at least one embodiment, a delivery system comprises a balloon having a plurality of protrusions or herniations with a stent disposed about the balloon. In some embodiments, at least one of the plurality of protrusions or herniations deploys at least one side branch of the stent disposed about the balloon.

These and other embodiments which characterize the invention are pointed out with particularity in the claims annexed hereto and forming a part hereof. However, for further understanding of the invention, its advantages and objectives obtained by its use, reference can be made to the drawings which form a further part hereof and the accompanying descriptive matter, in which there is illustrated and described an embodiments of the invention.

BRIEF DESCRIPTION OF THE SEVERAL VIEWS OF THE DRAWING(S)

A detailed description of the invention is hereafter described with specific reference being made to the drawings.

FIG. 5a-g are examples of different configurations for the undulating member and the side branch opening defined by the undulating member.

Figure 1:
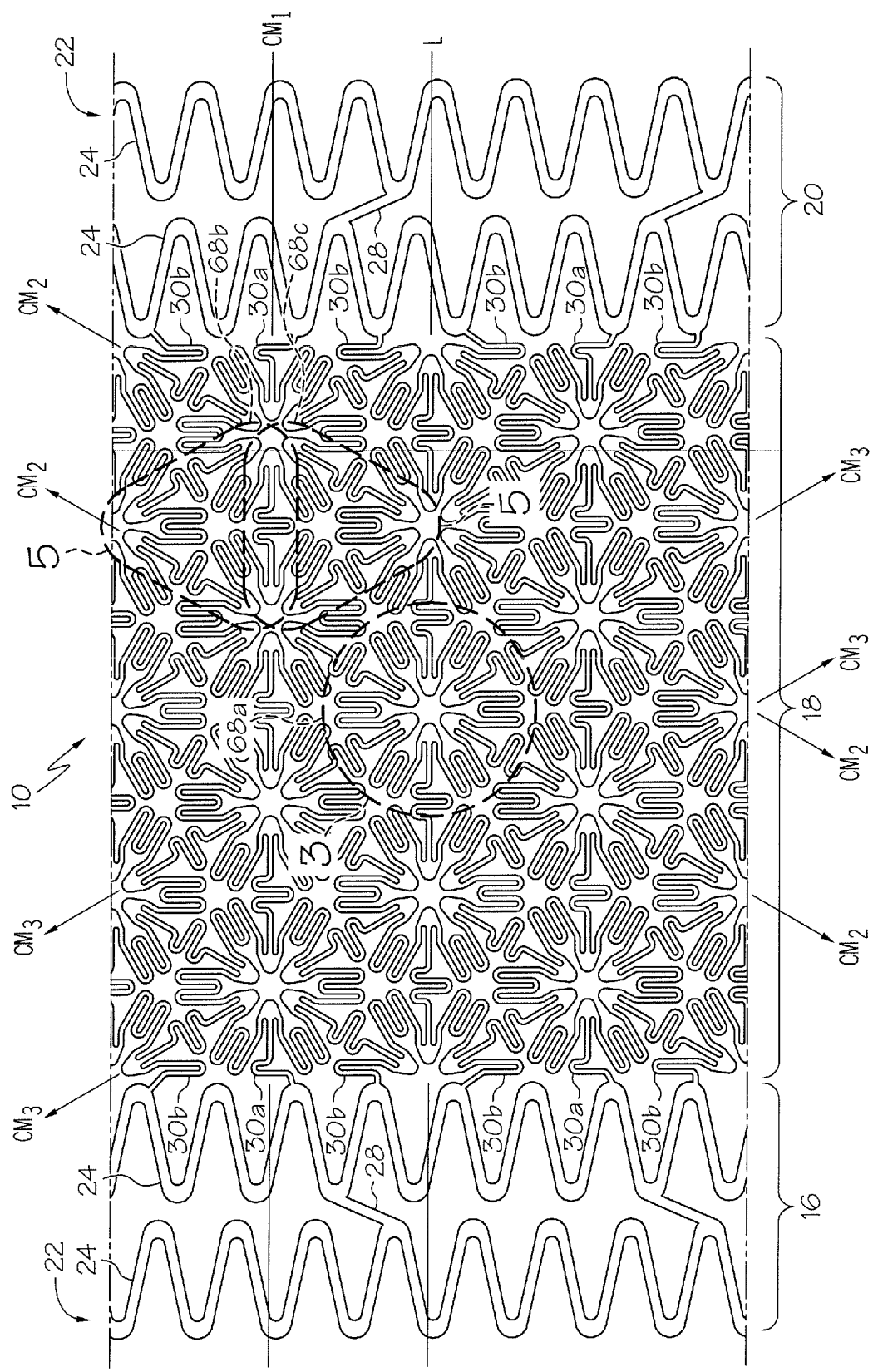
FIG. 1 is a "rolled out" or plan view of a stent embodiment with a plurality of first potential side branches and a plurality of second potential side branches.
Figure 6:
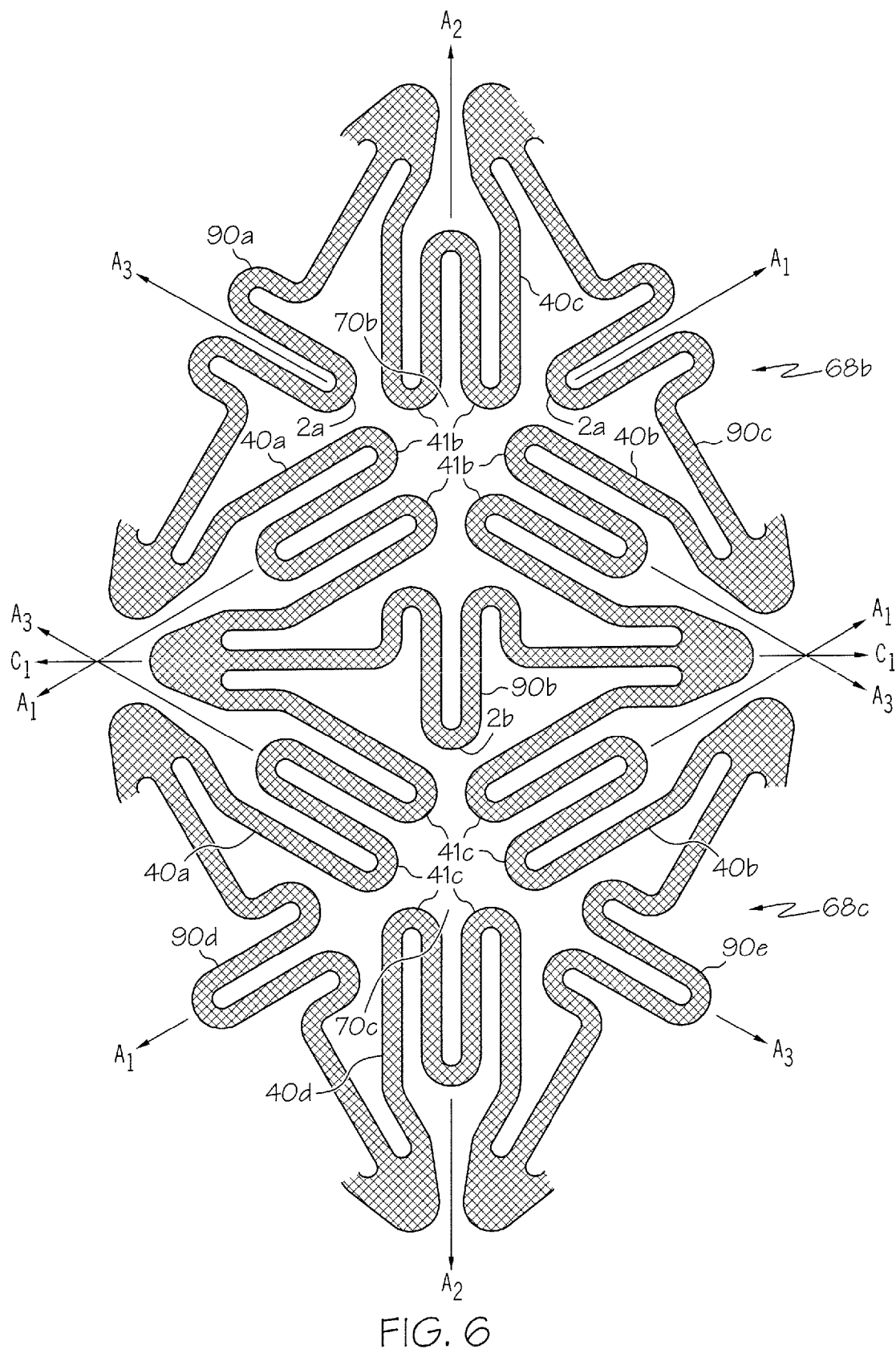

FIG. 6 is an enlarged view of the second potential side branch of FIG. 1, in a first orientation and a second orientation.

Figure 7:
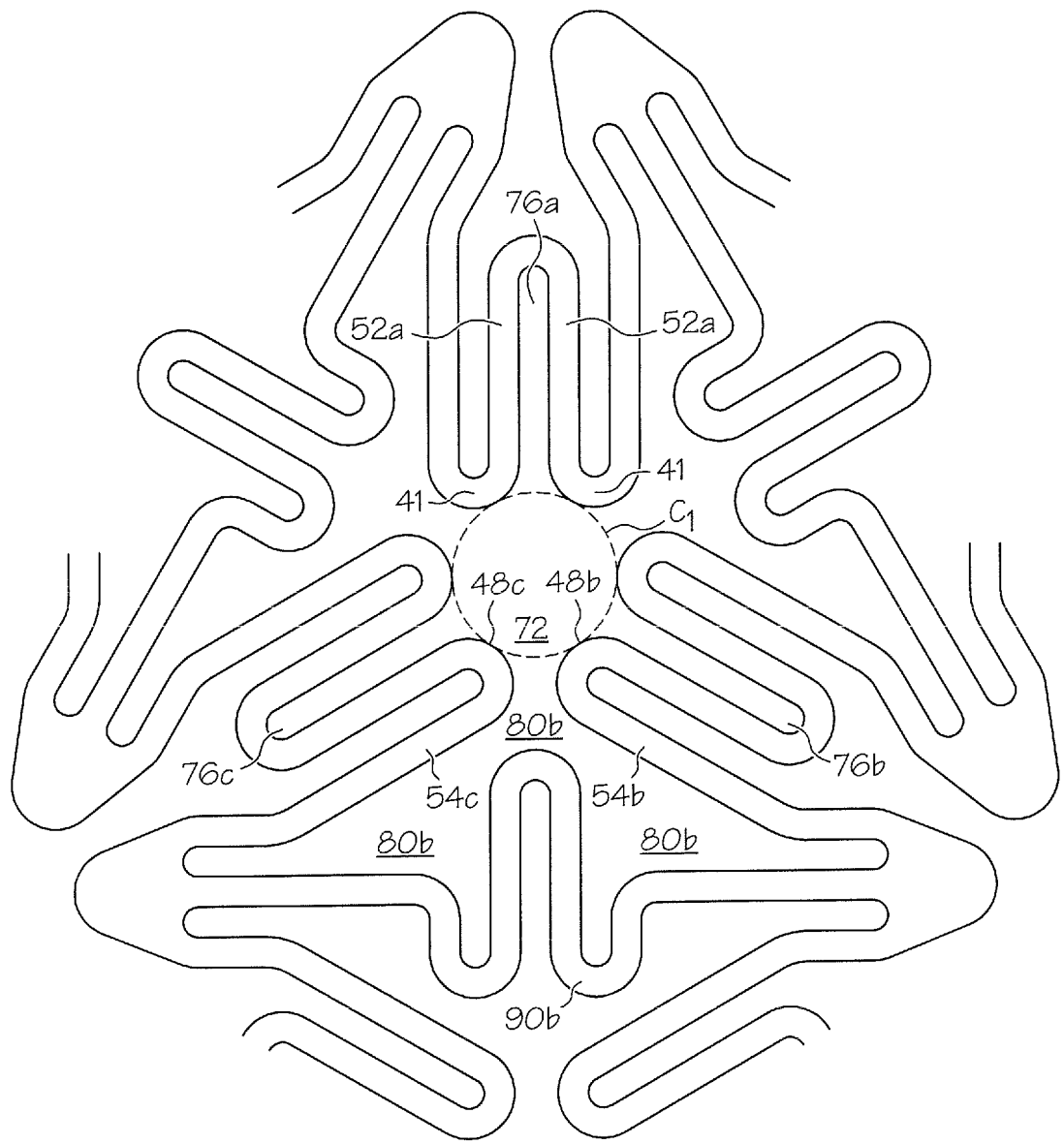

FIG. 7 is an enlarged view of the second potential side branch showing the different regions of the side branch opening.

Figure 8:
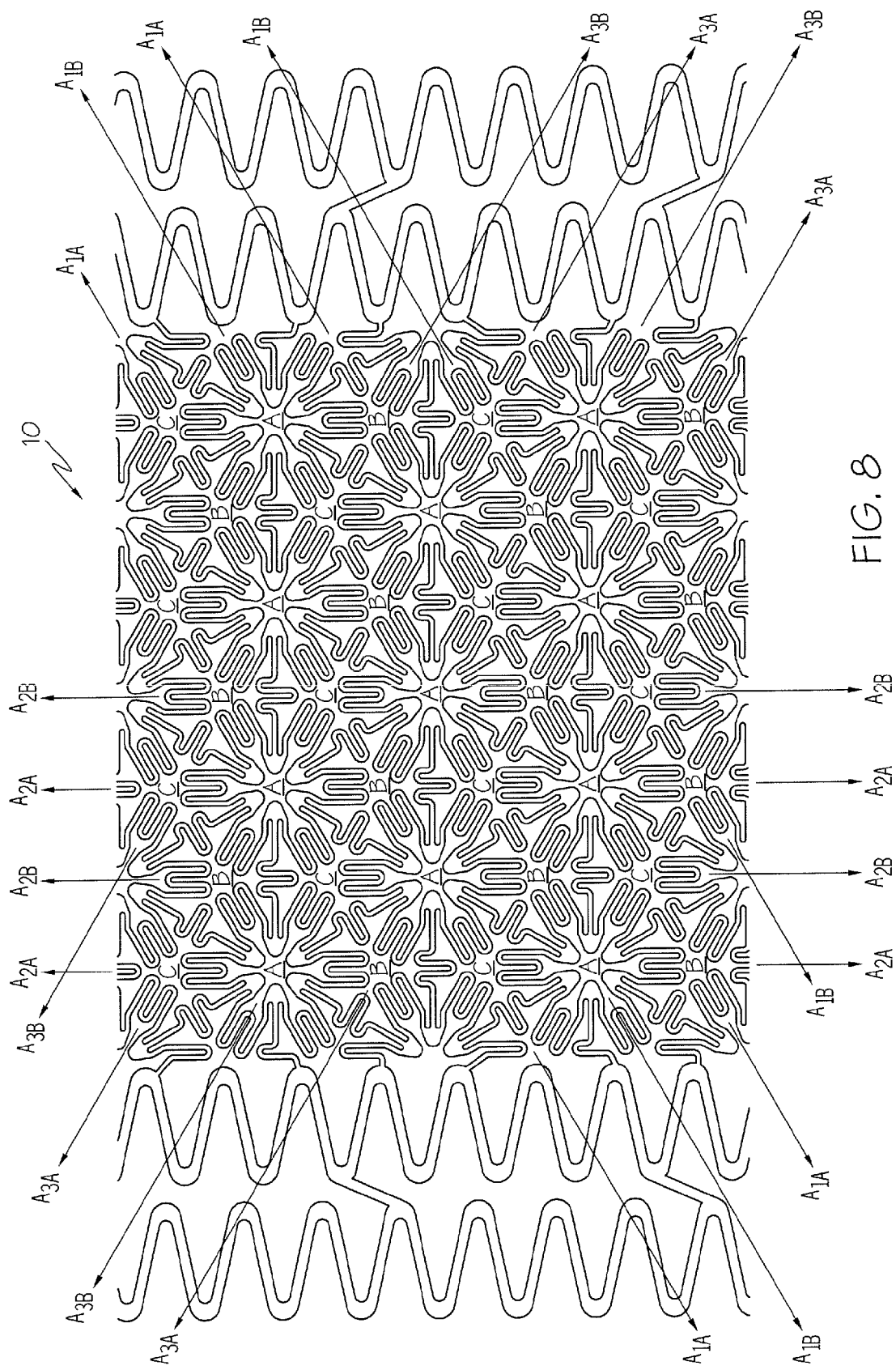

FIG. 8 illustrates axes of the second and third cell types in the stent of FIG. 1.

Figure 9:
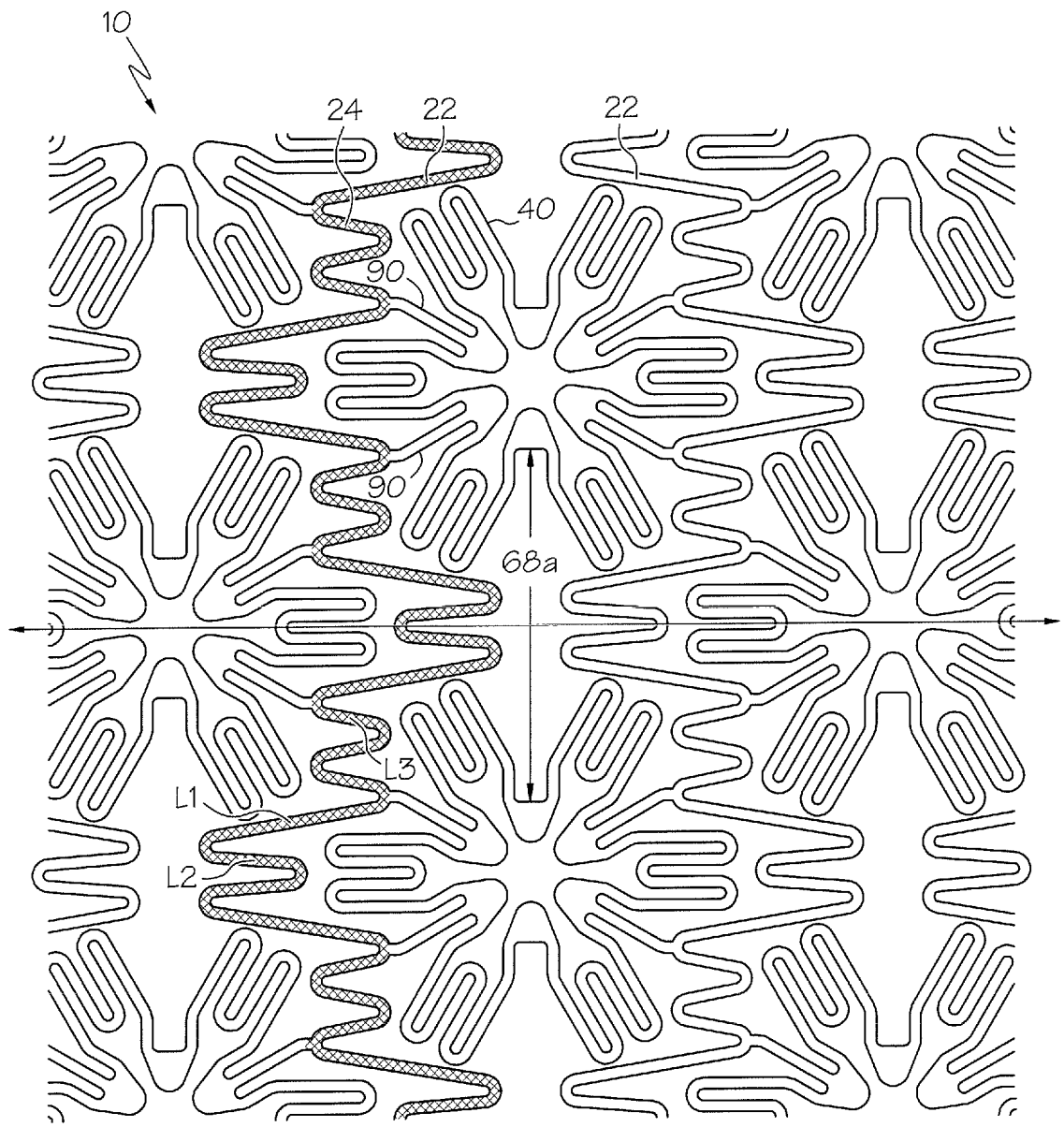
Figure 10A:
Figure 10B:
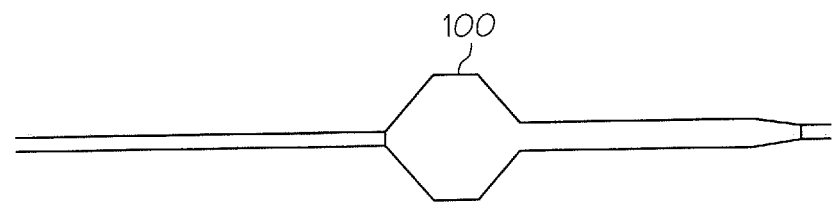
Figure 10C:
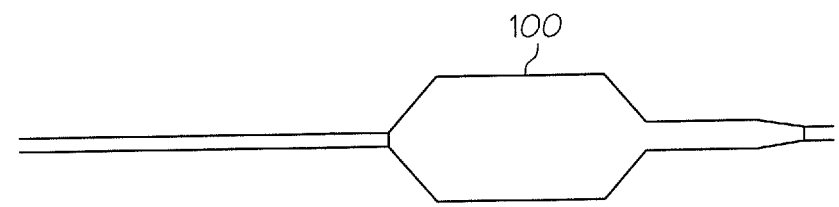
Figure 10D:
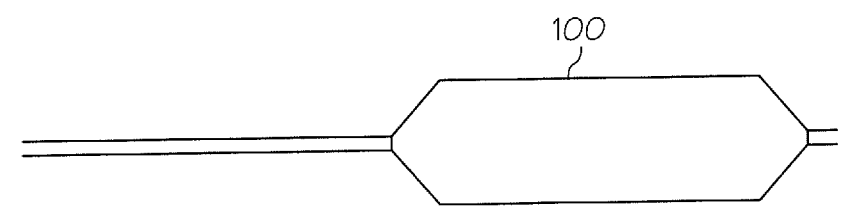

FIG. 9 is a "rolled out" or plan view of a stent embodiment with a plurality of potential side branches, each having the same configuration.

FIG. 10A-D is a side view of a balloon that progressively inflates from the proximal end to the distal end.

Figure 11:
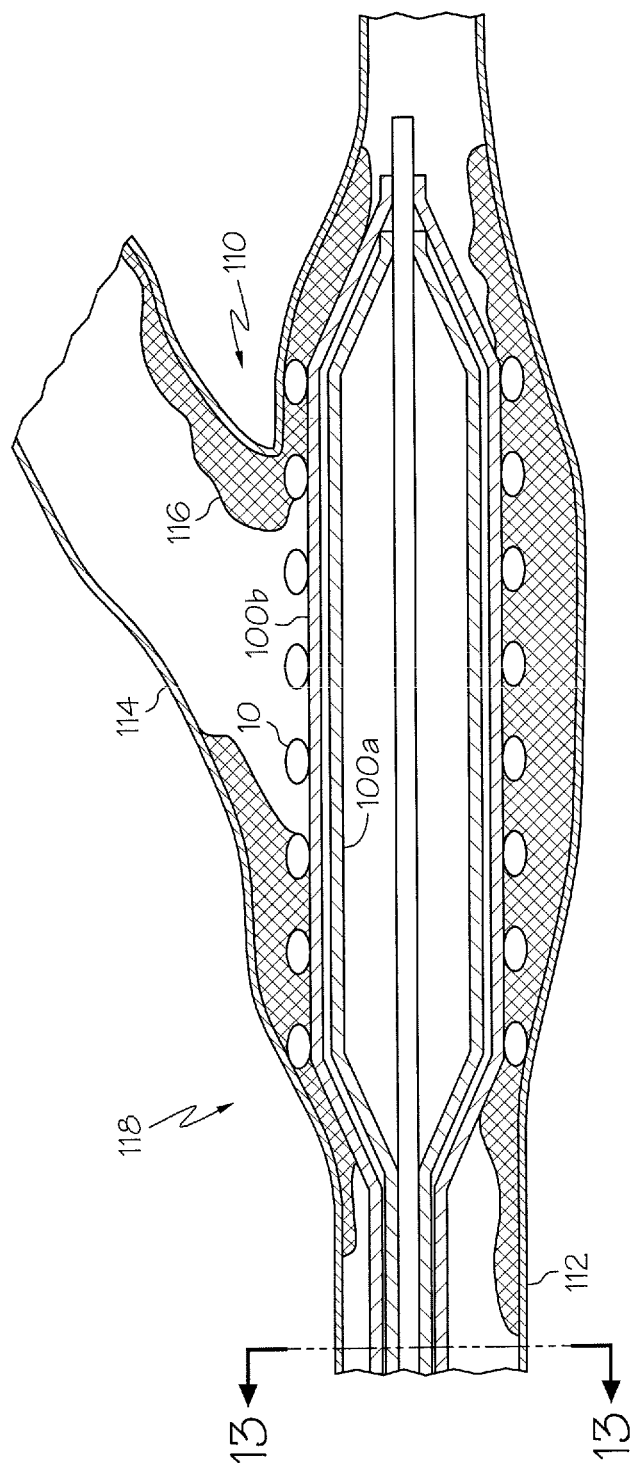

FIG. 11 is a longitudinal cross section of a dual lumen balloon with the inner balloon inflated.

Figure 12:
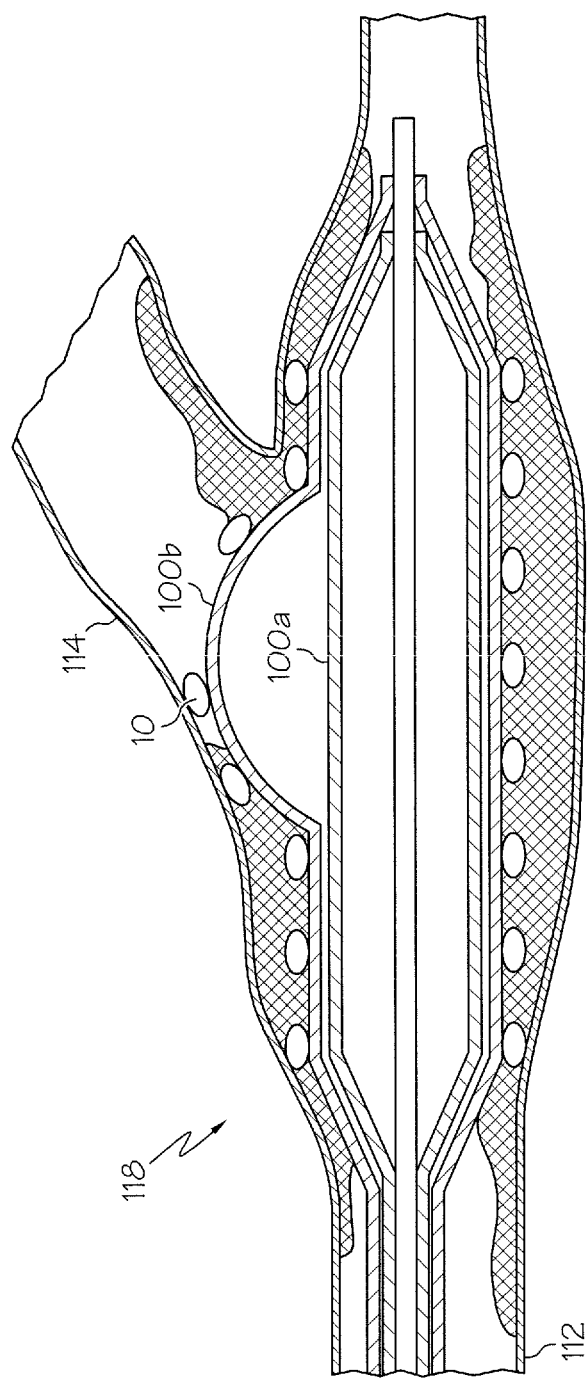

FIG. 12 is the dual lumen balloon of FIG. 11 with the outer balloon inflated.

Figure 13:
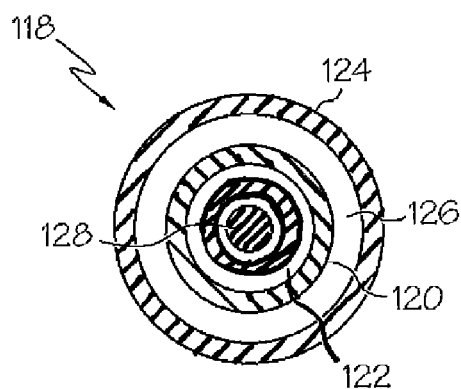

FIG. 13 is a cross-section of the dual lumen balloon of FIG. 11.

Figure 14:
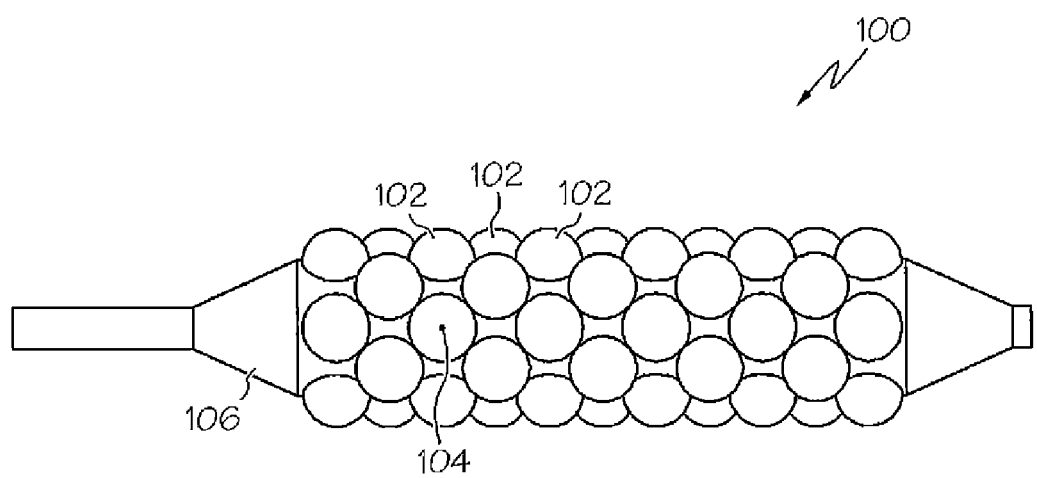

FIG. 14 illustrates a balloon with a plurality of protrusions.

Figure 15:
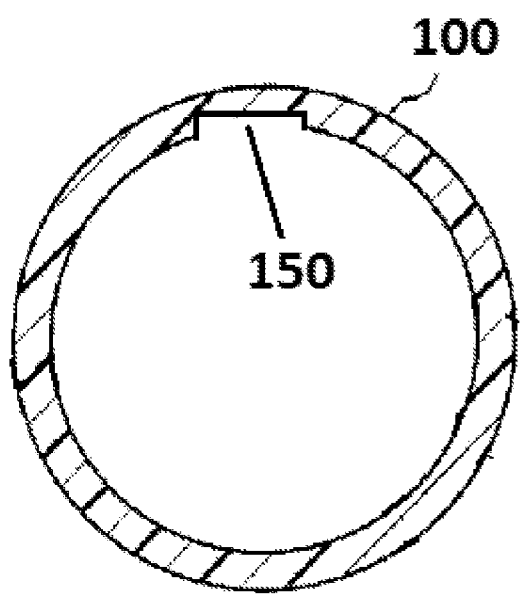

FIG. 15 is a cross-sectional view of a balloon with a channel molded on its interior surface.

DETAILED DESCRIPTION OF THE INVENTION

While this invention may be embodied in many different forms, there are described in detail herein specific embodiments of the invention. This description is an exemplification of the principles of the invention and is not intended to limit the invention to the particular embodiments illustrated.

Figure 3:
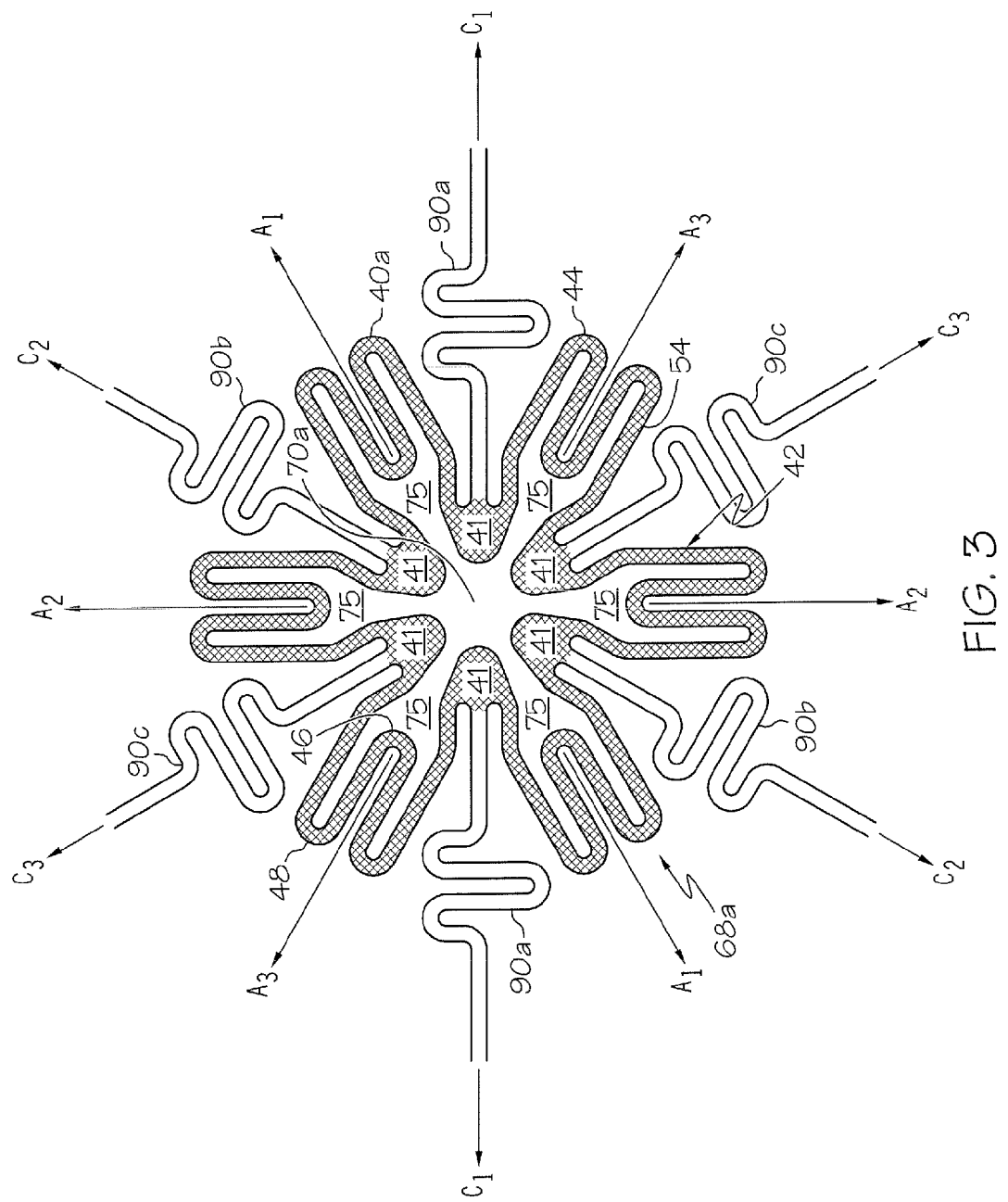
FIG. 3 is an enlarged view the first potential side branch of FIG. 1.
Figure 4:
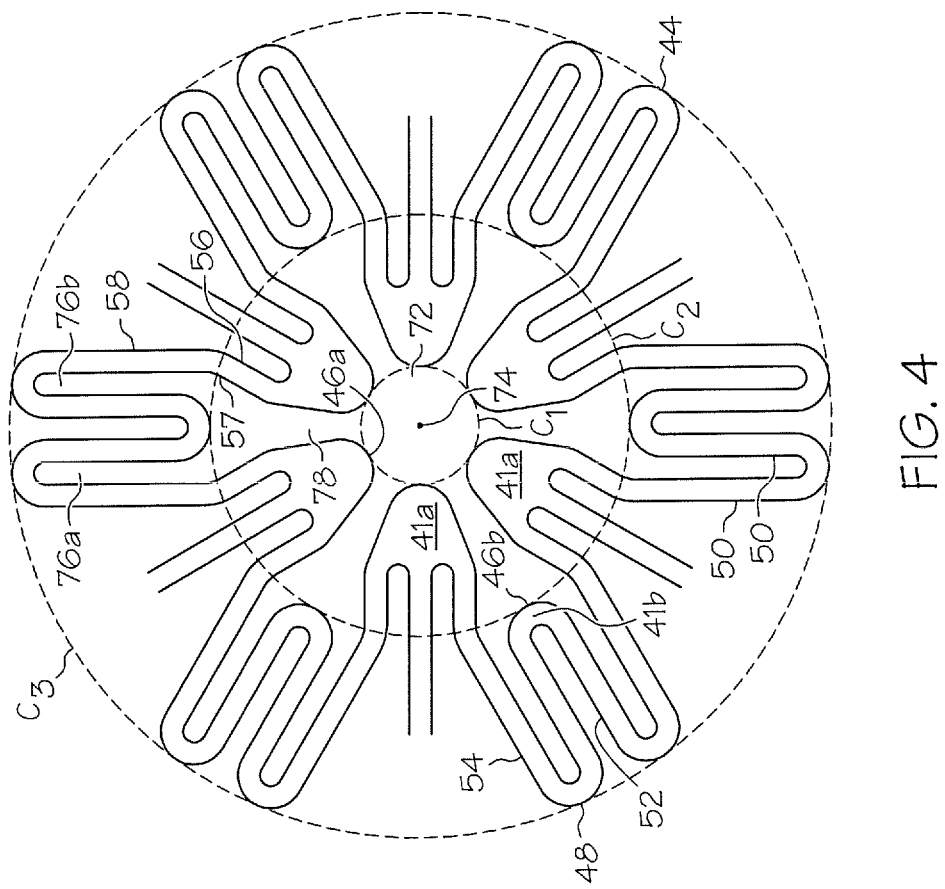
FIG. 4 is the enlarged view of FIG. 3 illustrating the relationship of portions of the first potential side branch in relation to three reference circles.
Figure 5A:
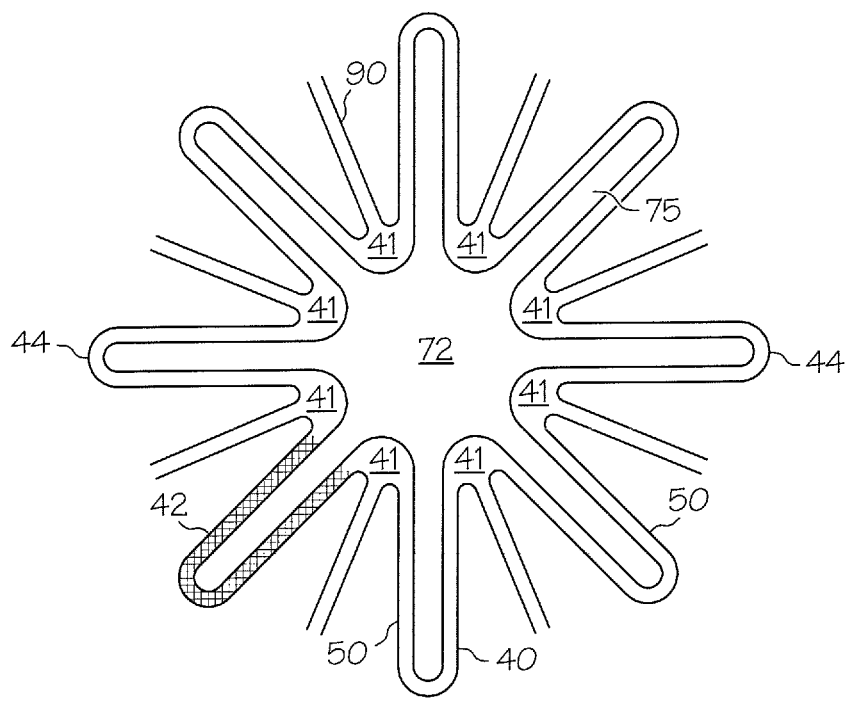
Figure 5B:
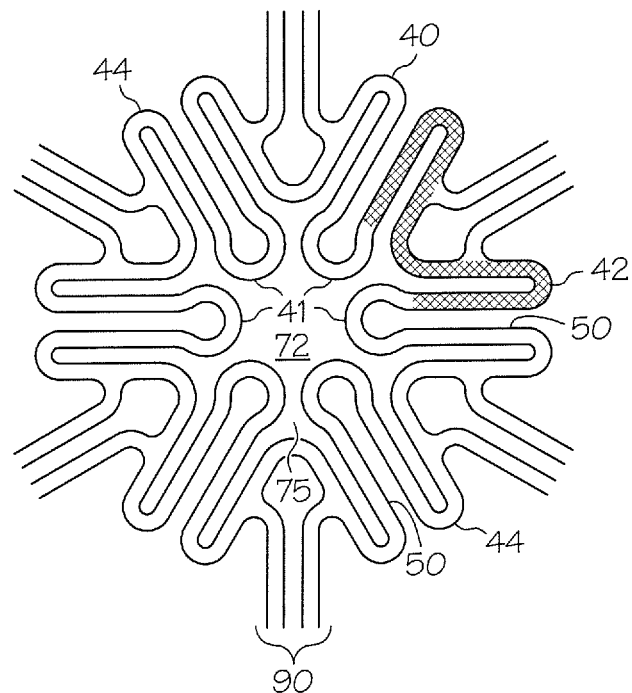
Figure 5C:
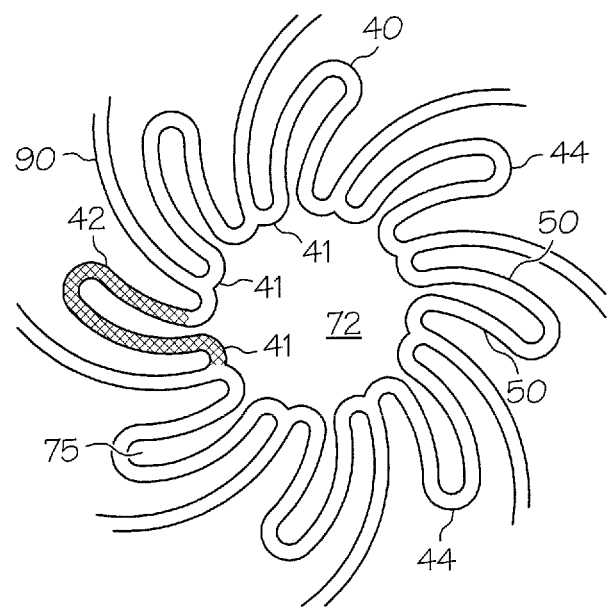
Figure 5D:
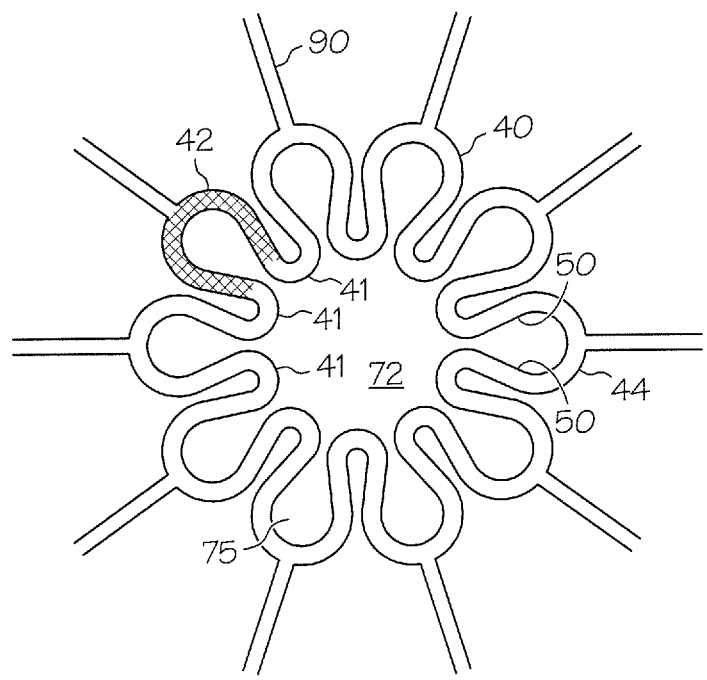
Figure 5E:
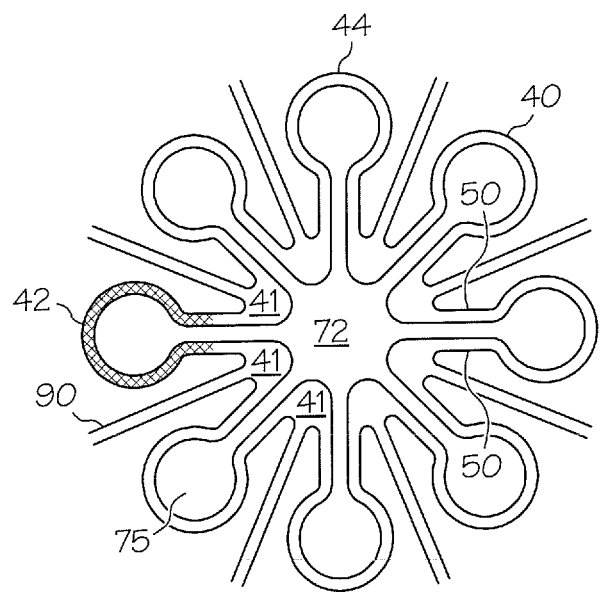
Figure 5F:
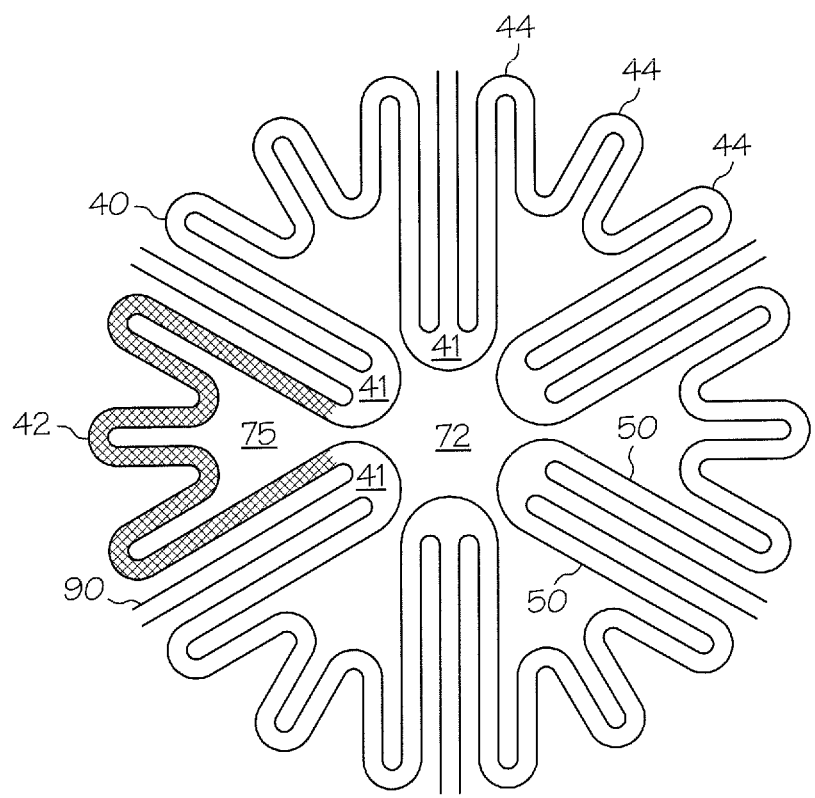
Figure 5G:
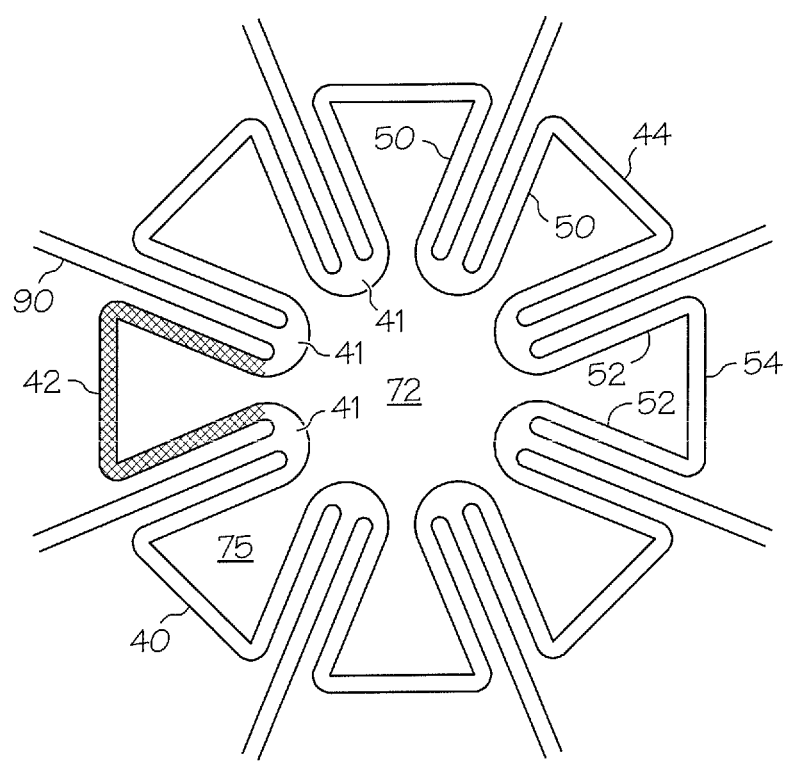

For the purpose of this disclosure, like reference numerals in the figures shall refer to like features unless otherwise indicated. Note that identifiers, e.g. a, used in FIGS. 1 and 3-4 are not intended to be the same in FIGS. 6-7. Thus, for example, connecting member 90a in FIG. 3 is not the same as connecting member 90a in FIG. 6. As used in this application, an oblique angle is any angle between 0 and 180 degrees and includes 90 degrees.

Although the figures in this application show the stent 10 in a flat, plan view, in use, the stent 10 has a tubular body. The wall of the tubular body has curvature, therefore the members forming the tubular body, e.g. struts 24, serpentine members 40 etc., have the same curvature as the wall of the tubular body. In addition, the cells 70 defined by the members of the tubular body also have curvature because the cells 70 are defined by the wall of the stent 10.

As used in the application, the terms serpentine, undulating and zig-zag describe a winding course or pathway. Thus, a pathway with plurality of turns is undulating, serpentine or zig-zag. The turns of the pathway can be sharp, curved, and any combination thereof.

Figure 2:
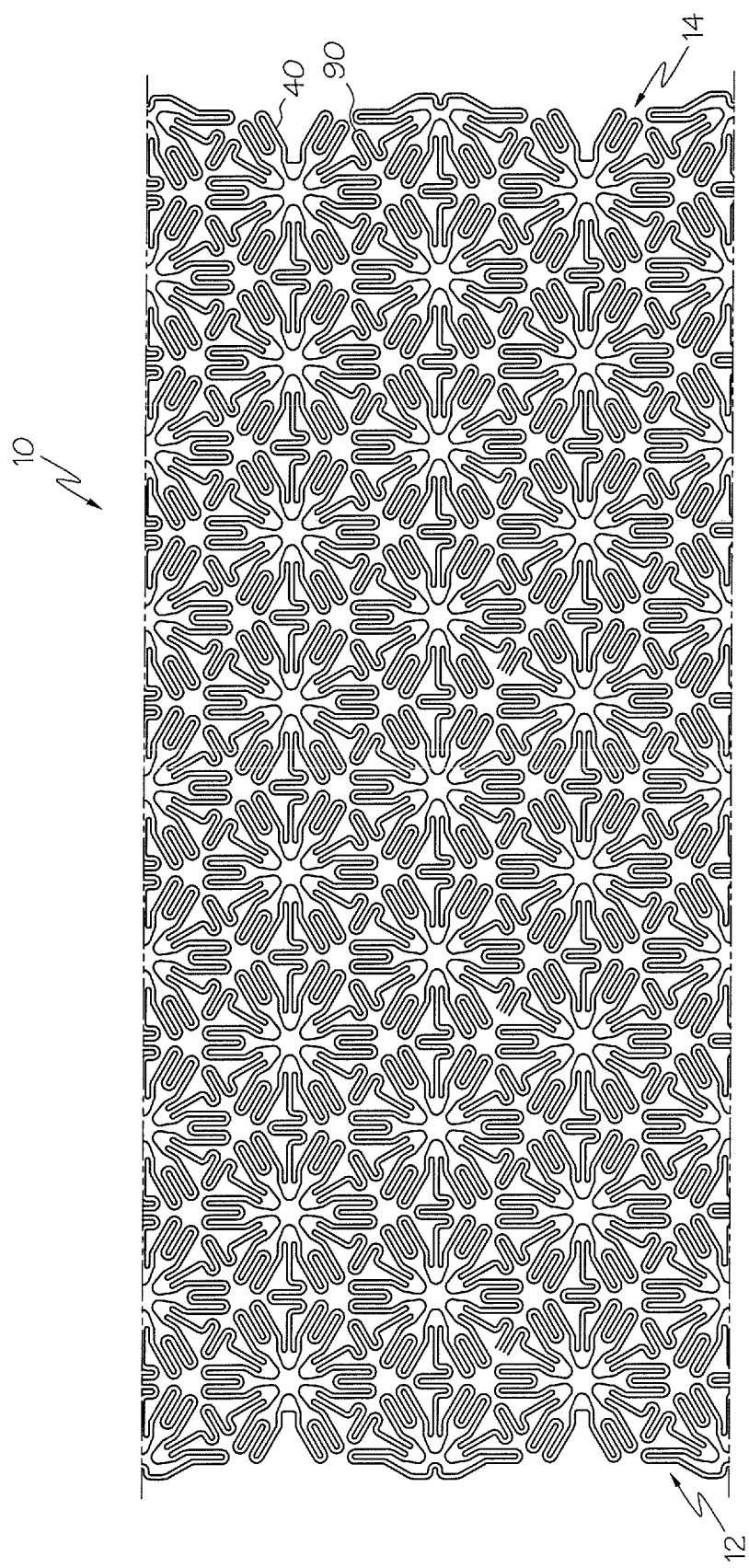
FIG. 2 is an example of a configuration for the end(s) of a stent comprising only a plurality of serpentine members and connecting members.

FIG. 1 is an embodiment of a stent 10 with a proximal section 16, a middle section 18 and a distal section 20. In some embodiments, the stent 10 comprises only a plurality of serpentine or undulating members 40 and a plurality of connecting members 90, as shown in FIG. 2. Thus, this stent 10 only comprises the middle section 18 of the stent shown in FIG. 1. Therefore, because the stent 10 would have the configuration if the middle section 18, the proximal and/or distal ends 12 of the stent 10 have a different configuration than the stent shown in FIG. 1.

In the stent embodiments shown in FIG. 1, the proximal and distal sections 22,26 of the stent 10 are comprised of circumferential bands 16 of 24. The proximal and distal sections 22,26 each have two circumferential bands 22 of struts 24 that are engaged to one another by connectors 28. The circumferential bands 22 of struts 24 of the proximal and distal sections 22,26 can have any configuration. For example, commonly assigned patent application Ser. No. 11/519,552, entitled Longitudinally Flexible Expandable Stent, hereby incorporated by reference in its entirety, has some non-limiting examples of configurations of circumferential bands 22 of struts 24 engaged by connectors 28. It is within the scope of the invention for the proximal and/or distal sections 22,26 to have any number of circumferential bands 22 of struts 24, for example, but not limited to, one, two, three, four, five, six or more circumferential bands of struts 24.

The middle section 18 of the stent 10 in FIG. 1 is engaged to the proximal and distal sections 16,20 by inter-section connectors 30. It is within the scope of the invention for the inter-section connectors 30 to have any configuration, including by not limited to, curvilinear, straight, zig-zag, and having at least on bend. It is within the scope of the invention for the inter-section connectors 30 to have only one configuration or to have more than one configuration.

As shown in FIG. 1, the inter-section connectors 30 comprise first inter-section connectors 30a and second inter-section connectors 30b. In this embodiment, the configuration of the first inter-section connector 30a is different from the configuration of the second inter-section connector 30b In some embodiments, the configurations of the first and second inter-section connectors 30a,b are the same. In some embodiments, the first inter-section connector 30a is a portion of a connecting member 90. In some embodiments, the second inter-section connector 30b is a portion of an undulating member 40. In at least one embodiment, adjacent second inter-section connectors 30b are two portions of the same undulating member 40.

In at least one embodiment, the middle section 18 of the stent 10 comprises a plurality of undulating or serpentine rings/members 40 and a plurality of connecting members 90. In FIG. 1, the middle section 18 has a plurality of undulating members 40 and a plurality of connecting members 90 that define a plurality of potential side blanches 68. A potential side branch 68 is a side branch 68 in an undeployed state. In an undeployed state, the potential side branch 68 forms a portion of the tubular wall of the stent 10. In a deployed state, the side branch 68 extends away from the tubular wall of the stent 10 at an oblique angle to the longitudinal axis (L) of the stent 10. If the potential side branch 68 has petals 41, the petals 41 extend from the tubular wall of the stent 10 at an oblique angle to the longitudinal axis (L) of the stent 10 thereby forming the side branch 68. Each potential side branch 68 defines a cell that becomes a side branch opening 70 when the side branch 68 is in a deployed state.

In some embodiments, at least one of the potential side branches 68 is in a deployed state. Thus, the stent 10 in this embodiment is a bifurcated stent 10. In other embodiments, none of the plurality of potential side branches 68 are in a deployed state. Thus, the stent 10 in this embodiment is a non-bifurcated stent 10.

Each potential side branch 68 has a configuration. FIGS. 5a-g have some non-limiting examples of different potential side branch 68 configurations which can be used. FIGS. 5a-g are derived from commonly assigned application Ser. No. 11/653,589, entitled Bifurcated Stent, and U.S. Patent Application No 2007/0225796 entitled Bifurcated Stent, both of which are hereby incorporated by reference in their entirety. In at least one embodiment, the member 40 of the potential side branch 68 is undulating or serpentine, as shown, for example, in FIG. 1. In at least one embodiment, the member 40 is not undulating, as shown, for example, in FIG. 5g.

In some embodiments, all the potential side branches 68 have the same configuration, as shown for example in FIG. 9, discussed in greater detail below. In other embodiments, the potential side branches 68 have more than one configuration. For example, in FIG. 1, some of the plurality of potential side branches 68 are first potential side branches 68a having a first configuration and some of the plurality of potential side branches 68 are second potential side branches 68b,c having a second configuration. The two different potential side branch 68 configurations of FIG. 1 are discussed in greater detail below.

The first potential side branch 68a in FIG. 1, is shown in greater detail in FIG. 3. The first potential side branch 68a has an undulating member 40 with a plurality of petals 41. For reference, the undulating member 40 in FIG. 3 is cross-hatched. The different potential side branch 68 configurations shown in FIGS. 5a-f also have an undulating member 40 with a plurality of petals 41. In some embodiments, a petal 41 is a region of the undulating member 40 that has a greater surface area than the other turns 44 of the undulating member 40, shown for example, in FIG. 3. In other embodiments, the petal 41 does not have a greater surface area than the other portions of the undulating member 40a, shown for example, in FIG. 6. In FIG. 3, the undulating member 40a has six petals 41. However, the undulating member 40 can have any number of petals 41. It is within the scope of the invention for the undulating member 40 to have one, two, three, four, five, six, seven, eight, nine, ten or more petals 41.

In at least one embodiment, the undulating member 40 comprises alternating petals 41a and linking members 42. As shown in FIG. 3 and FIGS. 5a-g, the linking member 42 comprises a plurality of members 50 and at least one turn 44. For reference, a linking member 42 of each undulating member 40 is emphasized by hatch-marking. It is within the scope of the invention for the linking member 42 to have one, two, three, four, five, six, seven, eight, or more turns 44. The turns 44 can be inner turns 46 or outer turns 48. In some embodiments, all of the members 50 of a linking member 42 are parallel to one another, shown for example, in FIG. 5a. In some embodiments, a linking member 42 comprises a plurality of members 50 and a plurality of turns 44, shown for example in FIG. 5b In some embodiments, a linking member 42 comprises a plurality of outer turns 48 and at least one inner turn 46, shown for example in FIG. 3. Each outer turn 48 engages a first member 52 to a second member 54. The at least one inner turn 46 comprises at least one first inner turn 46a and at least one second inner turn 46b, as shown in FIG. 4. Each second inner turn 46b engages two second members 54 together.

In some embodiments, the linking member 42 comprises a plurality of second petals 41b. In this embodiment, each of the second petals 41 is partially defined by a second inner turn 46b. As shown in FIG. 4, the second petals 41b have a different distance from the center point 74 than the first petals 41a The second petals 41b can be any distance away from the center point 74. When this potential side branch 68 forms a side branch 68, the first petals 41a will be a greater distance away from the tubular wall of the stent 10 than the second petals 41b.

In some embodiments, the plurality of members 50 comprises a plurality of fast members 52 and a plurality of second members 54. It is within the scope of the invention for the first and second members 52,54 to be either straight or to have at least one bend 57. In some embodiments, the first and second members 52,54 have different lengths, as shown, for example, in FIG. 4. In other embodiments, the first and second members 52,54 have the same length, as shown, for example, in FIG. 5b. In at least one embodiment, the first members 52 of a linking member 42 are at an oblique angle to the second member 54, as shown, for example, in FIG. 5g.

As shown in FIG. 4, each of the second members 54 has a first section 56 and a second section 58. There is a bend 57 between the first section 56 and the second section 58. In this embodiment, the first section 56 of the second member 54 is engaged to the petal 41 and the second section 58 of the second member 54 is engaged to the outer turn 48. In some embodiments, adjacent second members 54 are mirror images to one another. Adjacent second members 54 include, for example, second members 54 engaged to the same petal 41 or second members 54 defining a portion of the arms 76 of the bident region 75, described in greater detail below.

In at least one embodiment, the undulating member 40 comprises a plurality of sections, each section comprising the following sequence of elements: a petal 41 (the petal 41 comprising a primary inner turn), a primary first member 52, a primary outer turn 48, a primary second member 54, a secondary inner turn 46b, a secondary second member 54, a secondary outer turn 48, and a secondary first member 52. The sections are arranged so that the first member 52 of one section is engaged to the petal 41 of the adjacent section. Although the undulating member 40 in FIG. 4 has six sections, it is within the scope of the invention for the undulating member 40 to have one, two, three, four, five, six, seven, eight, nine, ten, eleven, twelve or more sections.

In at least one embodiment, the undulating member 40 comprises a plurality of sections, each section comprising the following sequence of elements: a first petal 41a (the first petal 41a comprising a primary inner turn 46a), a primary first member 52, a primary outer turn 48, a primary second member 54, a second petal 41b (the second petal 41b comprising a secondary inner turn 46b), a secondary second member 54, a secondary outer turn 48, and a secondary first member 52. The sections are arranged so that the first member 52 of one section is engaged to the first petal 41a of the adjacent section.

In some embodiments, the undulating member 40 can be described in relation to the center point 74 of a center region 72 of the side branch opening 70, as shown in FIG. 4. The first inner turns 46a of the undulating member 40 are each located an equal distance away from the center point 74, and thus can be considered aligned around a first reference circle $C_1$. The second inner turns 46b of the undulating member 40 are each located an equal distance away from the center point 74, and thus can be considered aligned around a second reference circle $C_2$. The outer turns 48 of the undulating member 40 are each located an equal distance away from the center point 74, and thus can be considered aligned around a third reference circle $C_3$.

Because the reference circles $C_1$, $C_2$ and $C_3$ are centered upon the center point 74, reference circles $C_1$, $C_2$ and $C_3$ are concentric circles. In some embodiments, the same distance separates adjacent reference circles $C_1$, $C_2$ and $C_3$. Thus, the distance between $C_1$ and $C_2$ is the same as the distance between $C_2$ and $C_3$. In some embodiments, the distance between $C_1$ and $C_2$ is greater than the distance between $C_2$ and $C_3$. In some embodiments, the distance between $C_1$ and $C_2$ is smaller than the distance between $C_2$ and $C_3$. Note that when the flat pattern shown in the figures is in the shape of a tubular stent 10, the reference circles ($C_1$, $C_2$ and $C_3$) will be convex due to the curved surface of the tubular stent 10.

The undulating member 40 of the potential side branch 68a defines a first side branch opening 70a In this embodiment, the side branch opening 70a has a center region 72, with a center point 74, firm which six regions 75 extend. The regions 75 in this embodiment can be described as bident, as shown for example, in FIG. 3 or Y shaped, as shown for example, in FIG. 5b. However it is within the scope of the invention for the regions 75 to have any configuration FIGS. 5a-g show some non-limiting examples of configurations that the regions 75 can have, for example, but not limited to, circular, triangular and irregular shaped.

As shown in FIGS. 3-4, in this embodiment, the region 75 has a trunk 78 and a first arm 76a and a second arm 76b In this embodiment, each region 75 is defined by a pair of first members 52, a pair of outer turns 48 a pair of second members 54 and a second inner turn 46b. One first member 52, an outer turn 48 and a second member 54 define a first arm 76a of the region 75 while another first member 52, outer turn 48 and second member 54 define the second arm 76b of the region 75. In some embodiments, the first and second arms 76a,b of the region 75 are mirror images, as can be seen, for example, by axis $A_1$.

In at least one embodiment, the first and second arms 76a,b of the region 75 are parallel to one another, as shown, for example in FIG. 3. In some embodiments, a portion of both the fist and second arms 76a,b of the region 75 are parallel to one another. In at least one embodiment, the first and second arms 76a,b of the region 75 are at oblique angles to one another, as shown, for example, in FIG. 5b. In some embodiments, at least a portion of the first a second arms 76a,b of the region 75 are at oblique angles to one another.

In this embodiment, the six regions 75 form three pairs of regions 75, with each pair of legions 75 on an axis ($A_1$, $A_2$ and $A_3$) to the longitudinal axis (L) of the stent 10, as shown in FIG. 3. Thus, each side branch opening 70a has a six-fold symmetry. Side branch opening 70a is symmetrical because it has at least one axis of symmetry. Note that when the flat pattern, shown in FIG. 1 is in the form of a tubular stent 10, the axes ($A_1$, $A_2$ and $A_3$) are on the surface of the tubular stent 10 and thus, have curvature. In at least one embodiment, axis $A2$ is perpendicular to the longitudinal axis (L) of the stent 10. In at least one embodiment, the angle of axis $A_1$ to the longitudinal axis (L) of the stent 10 is equal to but opposite to the angle of axis $A_3$ to the longitudinal axis by) of the stent 10.

As shown in FIG. 3, this embodiment has six connecting members 90 engaged to the undulating member 40. Adjacent undulating members 40 are engaged to one another by at least one connecting member 90. It is within the scope of the invention for an undulating member 40 to have one, two, three, four, five, six, seven, eight, nine, ten or move connecting members 90 engaged thereto. In this embodiment, the number of connecting members 90 engaged to a particular undulating member 40 varies depending on its placement in the middle section 18. In this embodiment, an undulating member 40 is engaged to a minimum of one other undulating member 40 by a connecting member 90 to a maximum of six other undulating members 40.

In some embodiments, the connecting member 90 is engaged to the petal 41, as shown for example in FIG. 3. In other embodiments, the connecting member 90 is engaged to the outer turn 48 of a linking member 42, as shown for example in FIG. 5d. In at least one embodiment, the connecting member 90 is engaged to a strut member 50, as shown for example in FIG. 5b. It is within the scope of the invention for the connecting members 90 to have any configuration, including but not limited to, undulating, curvilinear, zig-zag, having at least one bend, or straight (having no bends). In some embodiments, the connecting members 90 have only one configuration. In other embodiments, the connecting members 90 have more than one configuration.

As shown in FIG. 3, in this embodiment, the connecting members 90 are undulating and can be divided into three groups 90a,90b,90c based on their axis or angle to the longitudinal axis (L) of the stent 10. The connecting members 90 can be at any angle, and thus have any axis, to the longitudinal axis (L) of the stent 10. Therefore, the number of axes depends upon the number of different angles to the longitudinal axis (L) of the stent 10. As used in this application, different angles include angles that are equal but opposite to one another. The connecting members 90 of the stent embodiment in FIGS. 1 and 3, have three axes, $CM_1$, $CM_2$ and $CM_3$. Axis $CM_1$ is parallel to the longitudinal axis (L) of the stent 10. Axes $CM_2$ and $CM_3$ are at an oblique angle to the longitudinal axis (L) of the stent 10. In at least one embodiment, axes $CM_2$ and $CM_3$ are equal but opposite angles to the longitudinal axis (L) of the stent 10. In some embodiments, the axis of a pair of connectors 90 divides the undulating member 40 in half and the two halves are mirror images, as shown, for example, in FIG. 3.

A second potential side branch configuration 68b is shown in FIG. 6. In this embodiment, two of the second potential side branches 68b and 68c are adjacent to, or abut, one another. In at least one embodiment, a portion of the second potential side branches 68b have a first orientation to the longitudinal axis of the stent 10 and a portion of the second potential side branches 68c have a second orientation to the longitudinal axis (L) of the stent 10. In this embodiment, the first and second orientations are equal but opposite orientations. Thus, if the second potential side branches 68b and 68c are viewed as having a triangular shape, the peaks of the two second potential side branches 68b and 68c are pointing in opposite directions. In some embodiments, the first and second orientations are at different oblique angles to the longitudinal axis (L) of the stent 10.

In some embodiments, both second side branch openings 70b and 70c are defined by alternating connecting members 90 and portions of undulating members 40, defining the regions 75 of the first side branch configuration 68a In this embodiment, side branch opening 70b is defined by connecting member 90a, a portion of undulating member 40a, connecting member 90b, a portion of undulating member 40b, connecting member 90c and a portion of undulating member 40c. Similarly, side branch opening 70c is defined by connecting member 90b, a portion of undulating member 40a, connecting member 90d, a portion of undulating member 40d, connecting member 90e and a portion of undulating member 40b. Thus, one connecting member 90, connecting member 90b, defines a portion of both side branch openings 70b and 70b. In addition, a first portion of undulating member 40a defines a portion of side branch opening 70b and second portion of undulating member 40a defines a portion of side branch opening 70c. Similarly, a first portion of undulating member 40b defines a portion of side branch opening 70b and a second portion of undulating member 40b defines a portion of side branch opening 70c.

In this embodiment, side branch openings 70b and 70c each have a center region 72, a first arm 76a, a second arm 76b, a third arm 76c, a first irregular shaped region 80a, a second irregular shaped region 80b, and a third irregular shaped region 80c, as shown in FIG. 7. Each arm 76 is defined by two first members 52 of an undulating member 40, a different undulating member 40 defining each arm 76. Each irregular shaped region 80 is defined by a portion of an outer turn 48 of a first undulating member 40a, a second member 54 of the first undulating member 40a, a connecting member 90, a second member 54 of a second undulating member 40b and a portion of an outer turn 48 of the second undulating member 40b. In some embodiments, each irregular shaped region 80 has one axis of symmetry. In other embodiments, each irregular shaped region 80 has no axes of symmetry.

In some embodiments, petals 41 are disposed about the center region 72 of the second potential side branch 68b/c. As shown in FIG. 6, six petals 41 are disposed about the center region 72, but it is within the scope of the invention for one, two, three, four, five, six, seven, eight, nine, ten, eleven, twelve or more petals 41 to be disposed about the center region 72 of the second potential side branch 68b/c. In this embodiment, each petal 41 is the outer turn 48 of the first side branch configuration 68a. Note that in this embodiment, the petals 41 of the first side branch configuration 68a have a different configuration than the petals 41 of the second side branch configuration 68b/c. It is within the scope of the invention for the different side branch configurations 68 to have the same petal 41 configuration.

In some embodiments, the second side branch configuration 68b/c can be described in reference to the center point 74. At least a portion of each of the petals 41 is located an equal distance away from the center point 74, and thus can be considered aligned around a first reference circle $C_1$, as shown in FIG. 7. In at least one embodiment, the second side branch opening 70b,c each have one axis of symmetry $A_2$. Axis $A_2$ is common to both side branch openings 70b,c. Side branch openings 70b,c are not symmetrical about axes $A_1$ and $A_3$. The $A_1$ axes of side branch openings 70b and 70c are parallel to one another. Similarly, the $A_3$ axes of side branch openings 70b and 70c are parallel to one another. In at least one embodiment, axis $A_1$ and axis $A_3$ are equal but opposite angles to the longitudinal axis (L) of the stent 10, which is parallel to axis $C_1$.

As shown in FIG. 1, this embodiment has forty-two (42) potential side branches 68. It is within the scope of the invention for the stent 10 to have any number of potential side branches 68. Thus, the stent 10 can have three to eighty four potential side branches 68. As shown in FIG. 1, this embodiment is an inter-nested arrangement or network of potential side branch openings where adjacent potential side branches 68 abut one another. The forty-two (42) potential side branches 68 are in seven (7) circumferential rows aligned along axes $A_{2A}$ and $A_{2B}$, which are perpendicular to the longitudinal axis of the stent 10, with each perpendicular circumferential row having six (6) potential side branches 68. In this embodiment, the potential side branches 68 can be described as being in a grid pattern.

As shown in FIG. 8, each perpendicular circumferential row has a repeating pattern of potential side branches 68: first potential side branch 68a (A)—second potential side branch in a first orientation 68b (B)—second potential side branch in a second orientation 68c (C). The circumferential position of a potential side branch 68 differs from the adjacent row, e.g. potential side branch 68a has a first circumferential position in perpendicular circumferential row $A_{2A}$ and a second circumferential position in perpendicular circumferential row $A_{2B}$. Similarly, potential side branch 68b has a first circumferential position in perpendicular circumferential row $A_{2A}$ and a second circumferential position in perpendicular circumferential row $A_{2B}$ and potential side branch 68c has a first circumferential position in perpendicular circumferential row $A_{2A}$ and a second circumferential position in perpendicular circumferential row $A_{2B}$. Thus, the perpendicular circumferential rows are offset from one another.

In at least one embodiment, the potential side branches 68 are aligned in a plurality of rows, as shown in FIG. 1. The rows can be either longitudinal rows or non-perpendicular circumferential rows. In some embodiments, the plurality of rows includes a plurality of first rows and a plurality of second rows. The plurality of first rows comprise alternating second side branches in a first orientation 68b and second side branches in a second orientation 68c. As shown in FIG. 1, one first longitudinal row is between line L, indicating the longitudinal axis of the stent 10, and axis $CM_1$, indicating the axis of a connecting member 90, and one second longitudinal low is aligned on axis $CM_1$. The plurality of second longitudinal rows comprise first side branches 68a engaged to adjacent first side branches 68a by connecting members 90. Similarly, one first non-perpendicular circumferential row is between two $CM_3$ axes and one second non-perpendicular circumferential row is aligned along a $CM_3$ axis. In addition, one first non-perpendicular circumferential row is between two $CM_2$ axes and one second non-perpendicular circumferential row is aligned along a $CM_2$ axis. As discussed above, the $CM_2$ axis has an angle to the longitudinal axis that is equal to, but opposite to, the $CM_3$ axis.

Additionally, this embodiment has non-perpendicular circumference rows of potential side branches 68 aligned along the $A_{1A}$ and $A_{3B}$ axes, as shown in FIG. 8. Each non-perpendicular circumferential row has a repeating pattern of potential side branches 68: first potential side branch 68a (A)—second potential side branch in a first orientation 68b (B)—second potential side branch in a second orientation 68c (C).

Note that the number of potential side branches 68 in a circumferential or longitudinal row depends upon the diameter of the stent 10, the size of the potential side branches 68, the distance between adjacent potential side branches 68, the longitudinal length of the section of the stent 10 containing the potential side branches 68 and any combination thereof.

A stent 10 which comprises a plurality of potential side branches 68 that each have the configuration, is shown in FIG. 9. In this embodiment, the potential side branch 68 has the configuration of the first potential side branch 68a of FIG. 1, described in detail above. As shown in FIG. 9, the plurality of first potential side branches 68a are in circumferential rows where the first potential side branches 68a in adjacent circumferential rows are circumferentially offset from one another. Note that a potential side branch 68a of a first circumferential row and a potential side branch 68a of a third circumferential row lie on a longitudinal axis, indicated by the arrow in FIG. 9.

Adjacent circumferential rows of first potential side branches 68a are engaged to a circumferential band 22 of struts 24 by connecting members 90. In this embodiment, two connecting members 90 engage each first potential side branch 68a to the circumferential band 22, however, it is within the scope of the invention for any number of connecting members 90 to engage a first potential side branch 68a to the circumferential band 22. Thus, the potential side branch 68 can be engaged to the circumferential band 22 by one, two, three, four, five, six, or more connecting members 90. Although the connecting member 90 in FIG. 9 is straight, it is within the scope of the invention for the connecting member 90 to have any configuration, including, but not limited to, straight, curvilinear, and zig-zag.

In at least one embodiment, the struts 24 forming the circumferential band 22 have a plurality of discrete lengths, as shown, for example, in FIG. 9. In this embodiment, the struts 24 have a first length (L1), a second length (L2) and a third length (L3), where the first length (L1) is greater than the second length (L2), which is greater than the third length (L3). In some embodiments, the first length (L1) is greater than the second and third lengths (L2,L3) and the second and third lengths (L2,L3) are the same length. In at least one embodiment, the circumferential band 22 has an overall zig-zag pathway about the circumference of the stent 10, as shown, for example in FIG. 9. In other embodiments, the circumferential band 22 has an undulating or serpentine pathway about the circumference of the stent 10. In some embodiments, the circumferential band 22 is helical.

In at least one embodiment, the side branch of the stent 10 is deployed using a balloon catheter 118. In this embodiment, the stent 10 is first deployed in the main vessel in a manner known in the art. Then a guide wire and balloon 100 are advanced through an opening in the stent 10 into the side branch vessel. In some embodiments, the balloon 100 is inflated to open the side branch 68. In other embodiments, the balloon 100 progressively inflates from the proximal end to the distal end thereby deploying the side branch 68. In FIG. 10A-D, a progressively inflatable balloon 100 is illustrated transitioning from an uninflated state, FIG. 10A to fully inflated state, FIG. 10D.

A progressively inflatable balloon 100 can be formed, for example, by the use of specific fording techniques that control inflation (i.e., proximal to distal, distal to proximal, inside out, outside in, etc.); by gradient extrusion or intermittent layer coextrusion (ILC) techniques; variable heat formation of the balloon 100; or by variable wall thickness extrusions or molding of the balloon 100. In at least one embodiment, variable heat setting is used to produce a progressively inflatable balloon 100. In some embodiments, the balloon 100 is heat set into the folded configuration with more heat being applied at the proximal end of the balloon 100 than the distal end of the balloon 100. In this embodiment, the proximal end of the balloon 100 is stiffer than the distal end of the balloon 100 which causes the distal end of the balloon 100 to inflate before the proximal end of the balloon 100. In at least one embodiment, the balloon 100 has variable wall thickness with the proximal end of the balloon 100 having a thicker wall than the distal end of the balloon 100. In some embodiments, the variable wall thickness of the balloon 100 is produced by extrusion. In other embodiments, the variable wall thickness is produced by molding.

In at least one embodiment, the stent 10 is deployed in a body lumen using a balloon catheter 118 where the balloon 100 is a dual lumen balloon 100. Although the dual lumen balloon 100 is described in reference to a stent 10 to be deployed at a bifurcation, it the dual lumen balloon 100 can be used to deploy any type of stent/bifurcated stent 10, including but not limited to, stents 10 with auxetic stent geometry and stents 10 with self flaring designs.

As shown in FIG. 11, the dual lumen balloon 100 has an inner balloon 100a and an outer balloon 100b which are coextensive. FIG. 13 is a cross-section of the dual lumen balloon catheter 118 of FIG. 11. As shown in FIG. 13, the balloon catheter 118 has an inner shaft 120 which defines an inner inflation lumen 122 and an outer shaft 124 which defines an outer inflation lumen 126. The outer shaft 124 is disposed about the inner shaft 120 which is disposed about a guide wire 128.

In at least one embodiment, the inner balloon 100a and/or the outer balloon 100b has at least one channel molded therein. Thus, in this embodiment, the inner balloon 100a has channels molded on its exterior surface and/or the outer balloon 100b has at least one channel molded on its interior surface. In some embodiments, the channels allow unobstructed pressurization of the outer balloon 100b. A non-limiting example of a balloon with a channel molded in a surface is shown in FIG. 15 which is a cross-sectional view of a balloon 100 with a channel 150 molded on its interior surface.

In at least one embodiment, the inner balloon 100a is made of a material that allows the inner balloon 100a to be inflated at a high nominal pressure. In some embodiments, the inner balloon 100a is made of a non-compliant material. Examples of non-compliant material include, but are not limited to, polyethylene terephthalates, polyacrylenesulfide, and copolyesters.

In some embodiments, the inner balloon 100a is a monolayer of polymer, i.e. the inner balloon 100a comprises one polymer layer. In other embodiments, the inner balloon 100a comprises a plurality of polymer layers. In at least one embodiment, the layering of the polymer is varied along the length of the inner balloon 100a. In some embodiments, the composition of the polymer varies along the length of the inner balloon 100a. In other embodiments, the treatment of the inner balloon 100a is varied along the longitudinal length of the inner balloon 100a thereby varying the characteristics of the inner balloon 100a along the longitudinal length of the inner balloon 100a.

In at least one embodiment, the outer balloon 100b is made of a material that allows the outer balloon 100b to be inflated at a low nominal pressure. In some embodiments, the outer balloon 100b works at a pressure below that of the inner balloon 100a. In other embodiments, the outer balloon 100b is made of a compliant material Examples of compliant material include, but are not limited to, nylon, and polyamines. In other embodiments, the outer balloon 100b is made of a semi-compliant material. Examples of semi-compliant material include, but are not limited to, ethylene-vinyl acetate, polyvinyl chloride (PVC), olefin copolymers or homopolymers, polyethylenes, polyurethanes, crosslinked low density polyethylenes (PETs), highly irradiated linear low density polyethylene (LDPE), acrylonitrile polymers and copolymers, acrylonitrile blends and ionomer resins.

In some embodiments, the middle portion of the outer balloon 100b is constructed and arranged to be more compliant than either end portion. In some embodiments, the outer balloon 100b is a monolayer of polymer, i.e. the outer balloon 100b comprises one polymer layer. In other embodiments, the outer balloon 100b comprises a plurality of polymer layers. In at least one embodiment, the layering of the polymer is varied along the length of the outer balloon 100b. In some embodiments, the composition of the polymer varies along the length of the outer balloon 100b. In other embodiments, the treatment of outer balloon 100b is varied along the longitudinal length of the outer balloon 100b thereby varying the characteristics of outer balloon 100b along the longitudinal length of the outer balloon 100b. For example, as discussed above, the outer balloon 100b can be formed using variable heat, formed by gradient extrusion or intermittent layer coextrusion (ILC) techniques, or formed with a variable thickness wall.

The dual lumen balloon 100 can be manufactured in several ways. Note that with any of these manufacturing processes, the inner and outer balloons 100a,b are separate from one another, i.e. there is a space between the inner and outer balloons 100a,b, so that the two balloons 100a,b can be separately inflated by the inner inflation lumen 122 and the outer inflation lumen 126 respectively. Thus, the outer balloon 100b has a greater outer diameter than the inner balloon 100a in both balloons 100a,b are in an unexpanded state and when both balloons 100a,b are in an expanded or inflated state. In one embodiment, the inner and outer balloons 100a,b of the dual lumen balloon 100 each are fabricated using typical blow molding procedures and then subsequently threaded together. In another embodiment, the inner and outer balloons 100a,b are blow molded together with a nonstick or sacrifical layer between the inner and outer balloons 100a,b so that the inner and outer balloons 100a,b are separate balloons. In at least one embodiment, the inner and outer balloons 100a,b of the dual lumen balloon 10 are folded simultaneously using standard folding processes.

As briefly discussed above, a balloon catheter 118 with the dual lumen balloon 100 can be used to deliver the stent 10 to a bifurcation 110. When the stent 10 is at the bifurcation 110, the inner balloon 100a is inflated to a high nominal pressure. Expansion of the inner balloon 100a deploys the stent 10 in the main vessel 112, as shown in FIG. 11. In some embodiments, the lesion 116 is remodeled by the inner balloon 100a when it is expanded with high pressure.

After the inner balloon 100a has been inflated the outer balloon 100b is inflated to a low nominal pressure. Wherever the outer balloon 100b is not constrained by the main vessel 112, the outer balloon 100b distends/expands. Thus, when the dual lumen balloon catheter 118 is used at a bifurcation 110, at least a portion of the outer balloon 100b is distended when inflated with low pressure. Distension of the outer balloon 100b deploys at least one potential side branch(es) 68 into the side branch vessel(s) 114, as shown in FIG. 12. Note that because the outer balloon 100b will extend into any space, i.e. a side branch ostium, the outer balloon 100b can deploy multiple side branches 68 if there are multiple spaces/ostiums along the length of the outer balloon 100b. Also note that the dual lumen balloon 100 can also be used to deploy a stent at a location that does not have any ostiums or openings. Once the side branch(es) 68 are deployed, the balloon 100 is deflated and the balloon catheter 118 is removed from the body lumen. In at least one embodiment, another balloon catheter is used to further dilate the side branch(es) 68 into the side branch vessel(s) 114.

In some embodiments, the outer balloon 100b is molded smaller than the inflation size of the inner balloon 100a In this embodiment, a relief of pressure on both the inner and outer balloons 100a,b causes the outer balloon 100b to elastically collapse the inner balloon 100a. In some embodiments, the elastic collapse of the outer balloon 100b causes the balloon 100 to self-fold.

In at least one embodiment, the stent 10 is deployed in a body lumen using a balloon catheter where the balloon 100 has a plurality of protrusions or herniations 102. As used in this application, a protrusion or herniation 102 is a portion of the balloon 100 that is constructed and arranged to expand more than adjacent areas of the balloon 100. Some non-limiting examples balloons with protrusions or herniations are discussed in commonly assigned U.S. Pat. No. 6,258,099, entitled Stent Security Balloon/Balloon Catheter, and U.S. Patent Application Publication No 2005/0015108, entitled Catheter Balloon Systems and Methods, both of which are hereby incorporated in their entirety.

A non-limiting example of a balloon 100 with a plurality of protrusions 102 is shown in FIG. 14. Although the protrusions 102 are shown as having a substantially round configuration, the protrusion 102 can have any configuration, as shown in U.S. Pat. No. 6,258,099, hereby incorporated by reference in its entirety. Each protrusion 102 has a center point 104. The position of the protrusions 102 on the balloon 100 correspond with the locations of the potential side branches 68 of the stent 10. Thus, the center point 104 of the protrusion 102 is aligned with the center point 74 of the potential side branch 68, i.e. the two center points 104,74 have the same position. Each protrusion 102 has a size that is sufficiently large to deploy its corresponding potential side branch 68 into a deployed side branch 68. In at least one embodiment, the number of protrusions 102 equals the number of potential side branches 68.

When the stent 10 is delivered to a bifurcation site, the balloon 100 with the protrusions 102 is expanded. The amount of expansion of each of the protrusions 102 of the balloon 100 depends upon the position of the protrusion 102 relative to the ostium(s) of the side branch vessels. Thus, a protrusion 102 that is positioned next to an ostium of a side branch vessel will expand more than a protrusion 102 positioned next to the vessel wall because the vessel wall limits the expansion of the protrusion 102. A potential side branch 68 aligned with an ostium of a side branch vessel becomes a side branch 68 upon the expansion of the protrusion 102, which is able to expand to its fullest extent because a vessel wall is not preventing expansion of the protrusion 102, which deploys the side branch 68.

The deployment mechanism described above and the fact that the stent 10 has a plurality of potential side branches 68 and an equal number of protrusions 102 means that the stent 10 can be deployed at a bifurcation without the need for a second guidewire to align the side branch 68 with the ostium of the side branch vessel. In addition, because the wall of the vessel limits the expansion of the protrusions 102, the stent 10 can be used as a non-bifurcated stent 10.

In at least one embodiment, the balloon 100 comprises a compliant inner balloon 100a and a non compliant outer sheath 106 that has perforations. In this embodiment, the placement of the perforations can be tailored to the design of the stent 10 so that the perforations are aligned with the potential side branches 68. Examples of compliant and non-compliant materials are described above. When the balloon 100 is expanded, the diameter of the inner balloon 100a is constrained by the sheath 106, except at the perforations, where the inner balloon 100a extends through the perforations. Thus, when the inner balloon 100a is in an expanded state, the balloon 100 has a configuration similar to the balloon 100 shown in FIG. 14. Note that the perforations are sized so that the size of the inner balloon 100a extending through the perforation is sufficiently large enough to deploy a potential side branch 68. In this embodiment, the inner balloon 100a will not extend through a perforation that is next to the vessel wall. Deploying a bifurcated stent 10 using this balloon 100 is the same as described above in reference to a balloon 100 with protrusions 102.

The following numbered statements characterize at least one of the embodiments described above:

1. A stent, the stent having a tubular body comprising a first section, the first section comprising a plurality of expandable side branches abutting one another, the plurality of expandable side branches comprising a plurality of first side expandable branches and a plurality of second expandable side branches.

2. The stent of statement 1, the plurality of expandable first side branches having a first configuration and the plurality of expandable second side branches having a second configuration.

3. The stent of statement 2, the first configuration being different than the second configuration.

4. The stent of statement 2, the first configuration comprising a serpentine ring defining a side branch opening.

5. A stent, the stent having a tubular body comprising a first section, the first section comprising a first expandable side branch and a second expandable side branch, the first expandable side branch abutting the second expandable side branch.

6. The stent of statement 5, the first expandable side branch having a first configuration, the second expandable side branch having a second configuration, the first configuration being different than the second configuration.

7. A stent, the stent having a tubular wall defining at least two side branch openings, the at least two side branch openings being adjacent to one another and partially defined by at least one common member.

8. A stent, the stent having a tubular wall, the tubular wall defining an interested arrangement of at least two potential side branch openings.

The following numbered statements characterize at least one of the embodiments described above:

1. A stent, the stent having a tubular body, the tubular body having a wall, the wall having a first section comprising a plurality of serpentine rings and a plurality of connecting members, the plurality of connecting members engaging adjacent serpentine rings, the first section of the wall defining at least one first cell and at least one second cell, each of the at least one first cells being defined by one of the plurality of serpentine rings, each of the at least one second cells being defined by three of the plurality of connecting members and a portion of three of the plurality of serpentine rings.

2. The stent of statement 1, the at least one first cell having a center region, the center region having a plurality of secondary regions extending therefrom.

3. The stent of statement 4, each of the plurality of secondary regions having a trunk, a first arm and a second arm.

The following numbered statements characterize at least one of the embodiments described above:

1. A stent, the stent having a tubular body, the tubular body having a wall, the wall having a first section comprising a plurality of serpentine rings and a plurality of connecting members, the plurality of connecting members engaging adjacent serpentine rings, the first section of the wall defining a plurality of cells, the plurality of cells comprising at least one first cell and at least one second cell, each of the at least one first cells being defined by one of the plurality of serpentine rings, each of the at least one second cells being defined by three of the plurality of connecting members and a portion of three of the plurality of serpentine rings.

2. The stent of statement 1, the stent having a longitudinal axis, a first portion of the at least one second cells having a first orientation to the longitudinal axis, a second portion of the at least one second cells having a second orientation to the longitudinal axis, the first orientation opposite from the second orientation.

3. The stent of statement 1, the at least one second cells being arranged in at least one longitudinal row of the at least one second cells, the at least one second cells in a longitudinal row alternating between a first orientation and a second orientation.

4. The stent of statement 3, a connecting member partially defining two adjacent second cells.

5. The stent of statement 3, the plurality of serpentine rings being arranged in at least one longitudinal row, adjacent serpentine rings in a longitudinal row being engaged by a connecting member.

6. The stent of statement 5, the at least one longitudinal row comprising a first longitudinal row and a second longitudinal row, a serpentine ring of the first longitudinal row being engaged to a serpentine ring of the second longitudinal row by a first connecting member and a second connecting member.

7. The stent of statement 6, the first connecting member being at a first oblique angle to the longitudinal axis of the stent, the second connecting member being at a second oblique angle to the longitudinal axis of the stent.

8. The stent of statement 1, the stent having a longitudinal axis, the at least one second cells being arranged in circumferential rows, the at least one second cells in a circumferential row alternating between a first orientation and a second orientation, the circumferential rows being at an oblique angle to the longitudinal axis of the stent.

9. The stent of statement 8, a connecting member partially defining two adjacent second cells.

10. The stent of statement 8, the plurality of serpentine rings being arranged in at least one circumferential row, adjacent serpentine rings in a circumferential row being engaged by a connecting member.

11. The stent of statement 10, the at least one circumferential row comprising a first circumferential row and a second circumferential row, a serpentine ring of the first circumferential row being engaged to a serpentine ring of the second circumferential row by a first connecting member and a second connecting member.

12. The stent of statement 11, the first connecting member being at an oblique angle to the longitudinal axis of the stent, the second connecting member being horizontal to the longitudinal axis of the stent.

13. The stent of statement 8, the stent comprising at least two circumferential rows of first and second cells, each circumferential row comprising at least one unit of cells.

14. The stent of statement 13, each unit of the at least one unit of cells comprising:
   a first cell;
   a second cell in a first orientation; and
   a second cell in a second orientation;
   the first cell adjacent to the second cell opening in the first orientation, the second cell in the first orientation being adjacent to the second cell in the second orientation.

15. The stent of statement 14, the at least one unit of cells comprising a first unit and a second unit, the first cell of the first unit being adjacent to the second cell in the second orientation of the second unit.

16. The stent of statement 13, the at least two circumferential rows of cells comprising:
   a first circumferential row of cells; and
   a second circumferential row of cells;
   the first cell of a first unit of the first circumferential row of cells being circumferentially offset from the first cell of a first unit of the second circumferential row of cells.

The following numbered statements characterize at least one of the embodiments described above:

1. A stent, the stent having a tubular body, the tubular body having a wall, the wall having a first section comprising a plurality of serpentine rings and a plurality of connecting members, the plurality of connecting members engaging adjacent serpentine rings, the first section of the wall defining at least one first cell and at least one second cell, each of the at least one first cells being defined by one of the plurality of serpentine rings, each of the at least one second cells being defined by three of the plurality of connecting members and a portion of three of the plurality of serpentine rings.

2. The stent of statement 1, each of the plurality of serpentine rings comprising a plurality of first petals.

3. The stent of statement 2, each of the plurality of connecting members being engaged to one of the plurality of first petals, each first petal having only one connecting member engaged thereto.

4. The stent of statement 2, adjacent first petals engaged by a linking member.

5. The stent of statement 4, the linking member comprising a plurality of struts and a plurality of turns.

6. The stent of statement 5, the plurality of turns comprising at least one inner turn and at least one outer turn.

7. The stent of statement 6, each of the at least one first cells having a center point, the at least one inner turn comprising a first inner turn and a second inner turn, each of the first inner turns being a first distance away from the center point, and each of the second inner turns being a second distance away from the center point.

8. The stent of statement 7, the second distance being greater than the first distance.

9. The stent of statement 8, each of the outer turns being a third distance away from the center point, the third distance being greater than the second distance.

10. The stent of statement 5, the plurality of struts comprising at least one first strut and at least one second strut.

11. The stent of statement 10, the at least one first strut having at least one bend.

12. The stent of statement 10, adjacent first struts being mirror images.

13. The stent of statement 1, each of the plurality of serpentine rings comprising a plurality of sections, each section comprising:
 a first petal
 a primary first strut;
 a primary outer turn;
 a primary second strut;
 a primary inner turn;
 a secondary second strut;
 a secondary outer turn; and
 a secondary first strut;
 a first end the first petal being engaged to a first end of the primary first strut, a second end of the primary first strut being engaged to a first end of the primary outer turn, a second end of the primary outer turn being engaged to a first end of the primary second strut, a second end of the primary second strut being engaged to a first end of the primary inner turn, a second end of the primary inner turn being engaged to a first end of the secondary second strut, a second end of the secondary second strut being engaged to a first end of the secondary outer turn, a second end of the secondary outer turn being engaged to a first end of the secondary first strut.

14. The stent of statement 13, adjacent sections being arranged so that a second end of the secondary first strut of a first section is engaged to a second end of a first petal of an adjacent section.

15. The stent of statement 1, each of the plurality of second cells comprising:
 a center region;
 a first arm;
 a second arm;
 a third arm;
 a first irregular shaped region;
 a second irregular shaped region; and
 a third irregular shaped region;
 wherein each of the arms being defined by two second struts of one of the plurality of serpentine rings;
 wherein the plurality of serpentine rings comprising a first serpentine ring, a second serpentine ring and a third serpentine ring, the plurality of connecting members comprising a first connecting member, a second connecting member and a third connecting member,
  the first irregular shaped region being defined by the first connecting member, a primary first strut of the first serpentine ring, a portion of a first outer turn of the fist serpentine ring, a secondary first strut of the second serpentine ring, and a portion of a second outer turn of the second serpentine ring;
  the second irregular shaped region being defined by the second connecting member, a primary first strut of the second serpentine ring, a portion of a first outer turn of the second serpentine ring, a secondary first strut of the third serpentine ring, a portion of a second outer turn of the third serpentine ring; and
  the third irregular shaped region being defined by the third connecting member, a primary strut of the third serpentine ring, a portion of a first outer turn of the third serpentine ring, a secondary first strut of the first serpentine ring, and a portion of a second outer turn of the first serpentine ring.

16. The stent of statement 1, the tubular wall defining a first flowpath, each of the plurality of serpentine rings having a deployed configuration, the serpentine ring in the deployed configuration forming a first side branch, the first side branch being at an oblique angle to the tubular wall, the first side branch defining a second flowpath, the second flowpath in fluid communication with the first flowpath.

17. The stent of statement 16, each of the three connecting members and three serpentine rings defining each of the at least one second cells having a deployed configuration, the three connecting members and three serpentine rings in the deployed configuration forming a second side branch, the second side branch being at an oblique angle to the tubular wall, the second side branch defining a third flowpath, the third flowpath in fluid communication with the first flowpath.

18. The stent of statement 17, the stent having at least one first side branch.

19. The stent of statement 18, the stent further having at least one second side branch.

20. The stent of statement 17, the stent having at least one second side branch.

The inventive stents may be made from any suitable biocompatible materials including one or more polymers, one or more metals or combinations of polymer(s) and metal(s). Examples of suitable materials include biodegradable materials that are also biocompatible. By biodegradable is meant that a material will undergo breakdown or decomposition into harmless compounds as part of a normal biological process. Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol.

The inventive stents may be made of shape memory materials such as superelastic Nitinol or spring steel, or may be made of materials which are plastically deformable. In the case of shape memory materials, the stent may be provided with a memorized shape and then deformed to a reduced diameter shape. The stent may restore itself to its memorized shape upon being heated to a transition temperature and having any restraints removed therefrom.

The inventive stents may be created by methods including cutting or etching a design from a tubular stock, from a flat sheet which is cut or etched and which is subsequently rolled out or from one or more interwoven wires or braids. Any other suitable technique which is known in the art or which is subsequently developed may also be used to manufacture the inventive stents disclosed herein.

In some embodiments the stent, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments the at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

A therapeutic agent may be a drug ox other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular, features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending, directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. A catheter assembly comprising:
a catheter, the catheter comprising:
an inner shaft, the inner shaft defining an inner inflation lumen;
an outer shaft, the outer shaft disposed about the inner shaft, the outer shaft defining an outer inflation lumen;
a dual lumen balloon, the dual lumen balloon comprising:
an inner balloon, the inner balloon being made of non-compliant polymeric material, the inner balloon being in fluid communication with the inner inflation lumen;
an outer balloon, the outer balloon being disposed about and coextensive with the inner balloon, the entire outer balloon being made of a compliant polymeric material so that the entire balloon is compliant, the outer balloon being in fluid communication with the outer inflation lumen,
the dual lumen balloon having an unexpanded state when both the inner balloon and the outer balloon are uninflated; and
a stent, the stent disposed about the dual lumen balloon, the stent having a unexpanded state with an unexpanded diameter for delivery to an implantation site, the stent being radially expandable from the unexpanded state, the stent being in the unexpanded state when the dual lumen balloon is in the unexpanded state.

2. The catheter assembly of claim 1, wherein the inner balloon is configured to inflate at a first pressure and the entire outer balloon is configured to inflate at a second pressure, the second pressure being less than the first pressure.

3. The catheter assembly of claim 1, wherein the non-compliant polymeric material is selected from the group consisting of polyethylene terephthalates, polyacrylenesulfides and copolyesters and the compliant polymeric material is selected from the group consisting of nylon and polyamines.

4. The stent of claim 1, each of the plurality of circumferential bands of struts having a zig-zag pathway about the circumference of the stent.

5. The stent of claim 1, the stent having a circumferential axis, the plurality of serpentine rings comprising a first portion of serpentine rings and a second portion of serpentine rings, the first portion of serpentine rings positioned about the circumference of the stent on a first circumferential axis, the second portion of serpentine rings positioned about the circumference of the stent on a second circumferential axis, the first circumferential axis longitudinally separated from the second circumferential axis, one of the plurality of circumferential bands of struts positioned between the first and second portions of serpentine rings.

6. The catheter assembly of claim 1, wherein the unexpanded diameter of the stent is less than a diameter of the inner balloon when inflated for deployment of the stent.

7. The catheter assembly of claim 1, the dual lumen balloon having a first expanded state wherein only the inner balloon is in the inflated state, the stent being radially expandable to a deployed state from the unexpanded state for deployment at an implantation site, wherein the stent is in the deployed state when the dual lumen balloon is in the first expanded state.

8. The catheter assembly of claim 7, the dual lumen balloon having a second expanded state for expanding a side branch of the stent into a side branch lumen of an implantation site, the side branch being expanded after the stent is in the deployed state, wherein the outer balloon is inflated when the dual lumen balloon is in the second expanded state.

9. A catheter assembly comprising:
a catheter, the catheter comprising:
an inner shaft, the inner shaft defining an inner inflation lumen;
an outer shaft, the outer shaft disposed about the inner shaft, the outer shaft defining an outer inflation lumen;
a dual lumen balloon, the dual lumen balloon comprising:
an inner balloon, the inner balloon being made of non-compliant material, the inner balloon being in fluid communication with the inner inflation lumen;
an outer balloon, the outer balloon being disposed about and coextensive with the inner balloon, the outer balloon having a longitudinal length and being made of a compliant material, the compliant material having a compliancy that is the same along the longitudinal length of the outer balloon, the outer balloon being in fluid communication with the outer inflation lumen;

a stent with a side branch, the side branch forming a part of a wall of the stent when undeployed and extending away from an outer surface of the wall when deployed, the stent disposed about the dual lumen balloon, the stent and the side branch being separately deployable with the stent being deployed by the inner balloon and the side branch being deployed by the outer balloon and the stent having a tubular body, the stent having an unexpanded state and an expanded state, the tubular body having a wall, the wall having a first section comprising: a plurality of circumferential bands of struts; a plurality of serpentine rings, each serpentine ring being a side branch, each serpentine ring defining a first cell and a plurality of petals extending toward a center of the first cell when the side branch is in the undeployed state, the plurality of petals of the serpentine ring being positioned at an angle to the wall of the stent when the side branch is in the deployed state; and a plurality of connecting members engaging each serpentine ring to at least one of the plurality of circumferential bands so that each serpentine ring is engaged only to one or more circumferential bands.

10. A catheter assembly comprising:
a catheter, the catheter comprising:
 an inner shaft, the inner shaft defining an inner inflation lumen;
 an outer shaft, the outer shaft positioned around the inner shaft, the outer shaft defining an outer inflation lumen;
 a dual lumen balloon, the dual lumen balloon comprising:
  an inner balloon, the inner balloon inflatable at a first pressure, the inner balloon being in fluid communication with the inner inflation lumen;
  an outer balloon, the outer balloon being disposed around and coextensive with the inner balloon, the outer balloon having a longitudinal length extending from a first end to a second end, the longitudinal length of the outer balloon inflatable at a second pressure less than the first pressure, the outer balloon being in fluid communication with the outer inflation lumen; and
  a stent, the stent having an unexpanded diameter when positioned on the dual lumen balloon;
  wherein inflation of the inner balloon radially expands the stent to an expanded diameter greater than the unexpanded diameter.

11. The catheter assembly of claim 10, wherein inflation of the outer balloon expands a portion of the stent outward relative to an outer surface of the stent in the expanded diameter.

\* \* \* \* \*